(12) United States Patent  
Morishima et al.

(10) Patent No.: US 11,759,096 B2  
(45) Date of Patent: Sep. 19, 2023

(54) ENDOSCOPE

(71) Applicant: HOYA CORPORATION, Tokyo (JP)

(72) Inventors: Takayoshi Morishima, Tokyo (JP); Keiji Ito, Tokyo (JP); Kohei Iketani, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 184 days.

(21) Appl. No.: 17/047,442

(22) PCT Filed: Jun. 20, 2019

(86) PCT No.: PCT/JP2019/024525
§ 371 (c)(1),
(2) Date: Oct. 14, 2020

(87) PCT Pub. No.: WO2020/008900
PCT Pub. Date: Jan. 9, 2020

(65) Prior Publication Data
US 2021/0145265 A1  May 20, 2021

(30) Foreign Application Priority Data

Jul. 6, 2018 (JP) .................. 2018-129478

(51) Int. Cl.
*A61B 1/05* (2006.01)
*A61B 1/00* (2006.01)
(Continued)

(52) U.S. Cl.
CPC .......... *A61B 1/053* (2013.01); *A61B 1/00025* (2013.01); *A61B 1/0057* (2013.01);
(Continued)

(58) Field of Classification Search
CPC ............ A61B 1/00066; A61B 1/00089; A61B 1/0008; A61B 1/00103; A61B 1/00108; A61B 1/00101; A61B 1/00105
See application file for complete search history.

(56) References Cited

U.S. PATENT DOCUMENTS 5,662,588 A * 9/1997 Iida .................... A61B 1/00091
600/125
2002/0147447 A1 10/2002 Long
(Continued)

FOREIGN PATENT DOCUMENTS

CN 1708253 A 12/2005
EP 1723899 A1 11/2006
(Continued)

OTHER PUBLICATIONS

Office Action issued in Taiwanese Counterpart Patent Appl. No. 108121987, dated Nov. 3, 2020.
(Continued)

*Primary Examiner* — Aaron B Fairchild
(74) *Attorney, Agent, or Firm* — GREENBLUM & BERNSTEIN, P.L.C.

(57) ABSTRACT

An endoscope has an insertion portion with a simple configuration. The endoscope is an endoscope having an insertion portion and an operation unit connected to one end of the insertion portion. The insertion portion includes a tube provided with a plurality of channels penetrating in a longitudinal direction, an operation unit connected to one end of the tube, and a distal tip that covers another end of the tube and smoothly communicates with a part of the plurality of channels.

14 Claims, 30 Drawing Sheets

(51) Int. Cl.
  *A61B 1/005* (2006.01)
  *A61B 1/012* (2006.01)
(52) U.S. Cl.
  CPC ...... *A61B 1/00103* (2013.01); *A61B 1/00105* (2013.01); *A61B 1/00114* (2013.01); *A61B 1/00124* (2013.01); *A61B 1/012* (2013.01)

(56) References Cited

U.S. PATENT DOCUMENTS

| | | | |
|---|---|---|---|
| 2003/0088155 A1* | 5/2003 | Ishibiki | A61B 1/00089 600/127 |
| 2003/0225312 A1* | 12/2003 | Suzuki | A61B 17/00234 600/114 |
| 2004/0106853 A1 | 6/2004 | Moriyama | |
| 2004/0143162 A1* | 7/2004 | Krattiger | A61B 1/00101 600/129 |
| 2005/0075538 A1 | 4/2005 | Banik et al. | |
| 2005/0272975 A1 | 12/2005 | McWeeney et al. | |
| 2006/0200176 A1* | 9/2006 | Matsuno | A61B 1/00089 606/140 |
| 2006/0264708 A1 | 11/2006 | Horne | |
| 2007/0246506 A1* | 10/2007 | Hamazaki | A61B 1/0008 227/175.1 |
| 2013/0131452 A1* | 5/2013 | Kuroda | A61B 1/00071 600/136 |
| 2013/0172670 A1 | 7/2013 | Levy et al. | |
| 2018/0140171 A1* | 5/2018 | Yamaya | A61B 1/00062 |

FOREIGN PATENT DOCUMENTS

| | | |
|---|---|---|
| JP | 58-188423 | 11/1983 |
| JP | S63-014806 Y2 | 4/1988 |
| JP | 06-254047 | 9/1994 |
| JP | 06-254049 | 9/1994 |
| JP | H08-000543 A | 1/1996 |
| JP | H10-192222 A | 7/1998 |
| JP | 2001-299923 | 10/2001 |
| JP | 2004-261582 | 9/2004 |
| JP | 2006-116128 | 5/2006 |
| JP | 2006-149844 | 6/2006 |
| JP | 2008-043361 | 2/2008 |
| JP | 2009-148420 | 7/2009 |
| JP | 2010-158566 | 7/2010 |
| JP | 2013-123647 | 6/2013 |
| TW | 201438672 A | 10/2014 |
| WO | WO2005/094665 A2 | 10/2005 |

OTHER PUBLICATIONS

Office Action issued in Japanese Counterpart Patent Appl. No. 2020-528789, dated May 17, 2022.
Official Communication issued in European Patent Office (EPO) Patent Application No. 19831109.4., dated Feb. 22, 2022.
5th Office Action issued in Taiwanese Counterpart Patent Appl. No. 108121987, dated Aug. 9, 2022.
Official Communication issued in International Bureau of WIPO Patent Application No. PCT/JP2019/024525, dated Sep. 17, 2019.
Japanese Office Action dated Oct. 25, 2022, for corresponding Japanese Patent Application No. 2020-528789, together with an English translation.
Chinese Office Action dated May 12, 2023, for corresponding Chinese Patent Application No. 201980026696.6.
Office Action issued in Taiwanese Counterpart Patent Appl. No. 108121987, dated Apr. 21, 2022.

* cited by examiner

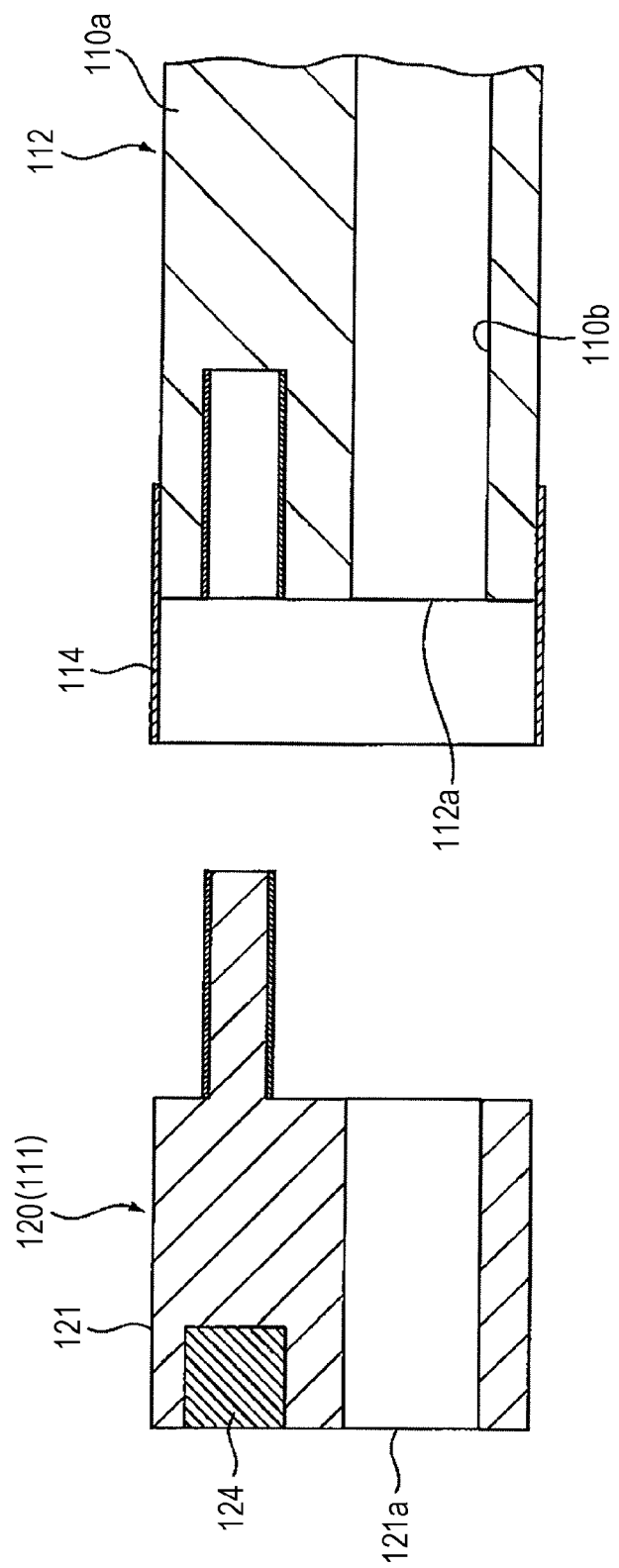

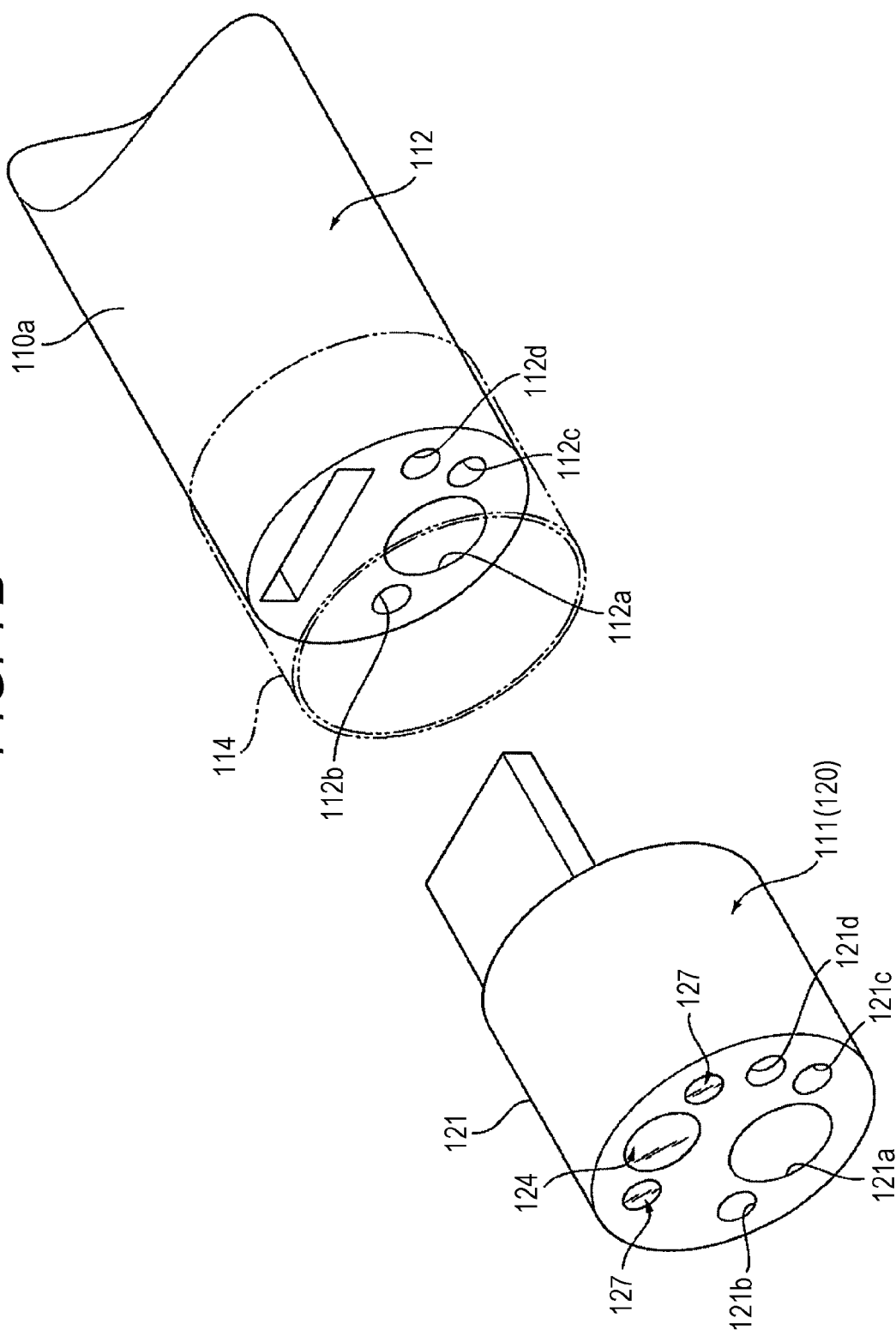

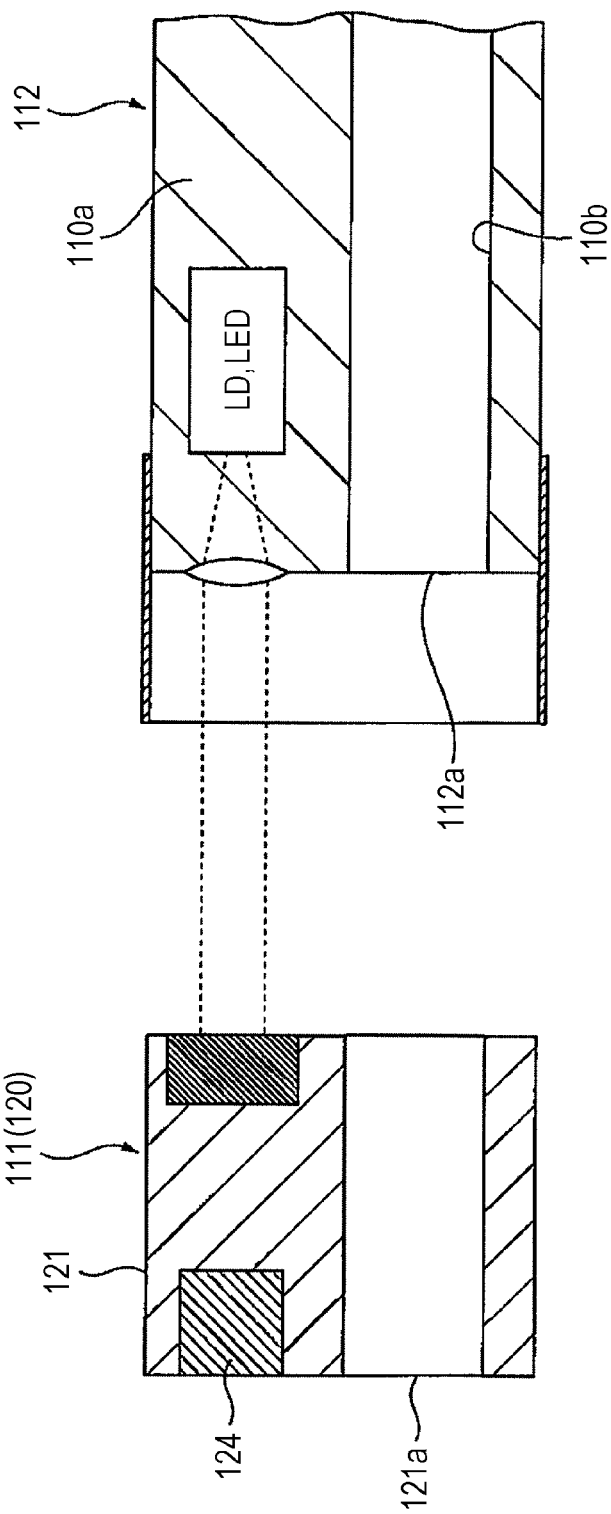

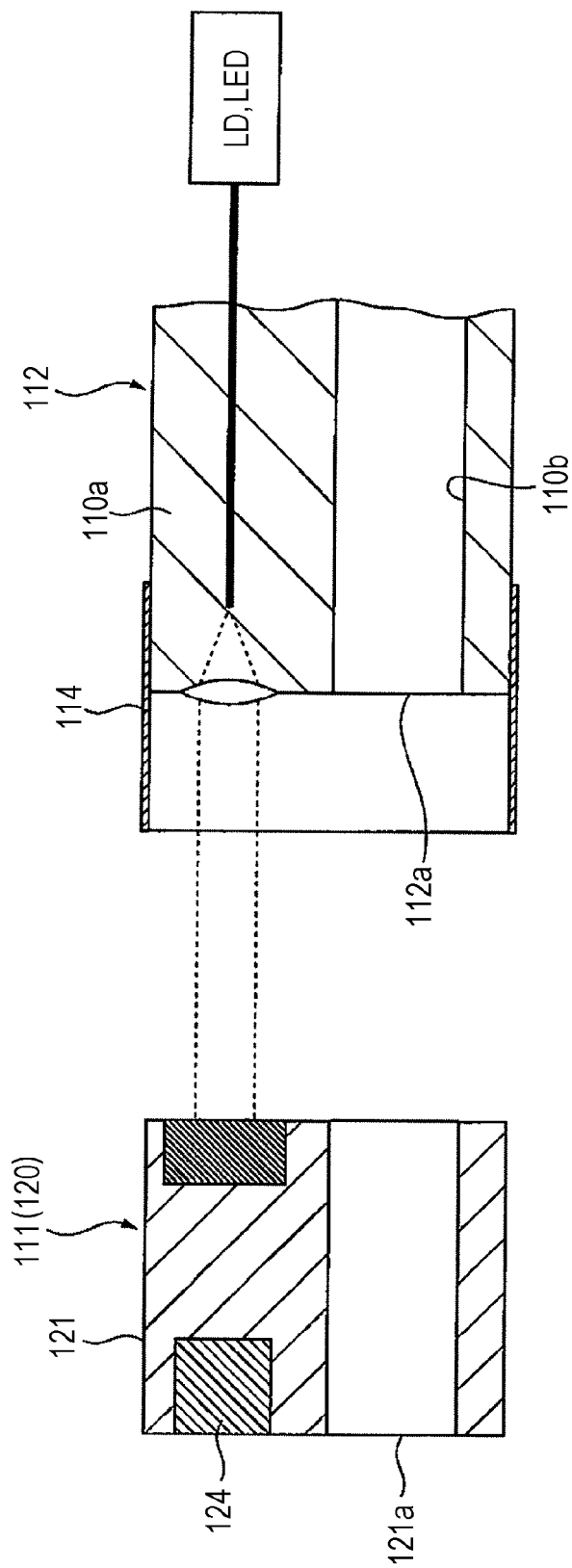

FIG. 11
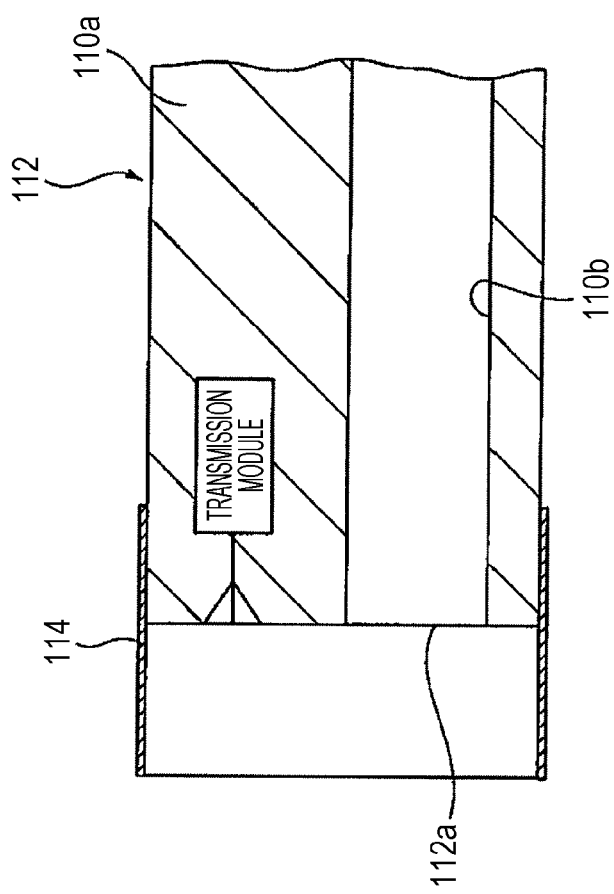
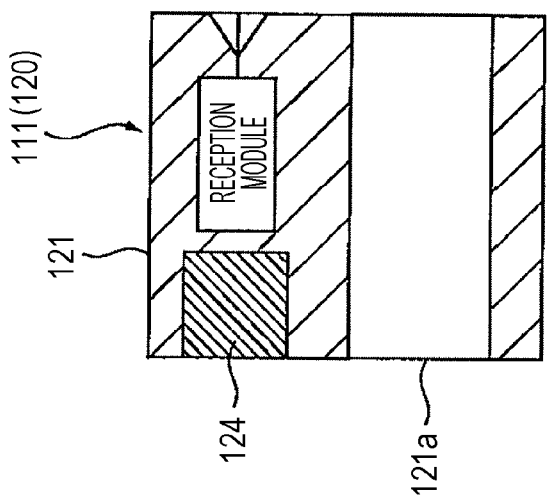

ENDOSCOPE

TECHNICAL FIELD

The present disclosure relates to an endoscope.

BACKGROUND ART

Conventionally, an invention relating to a flexible channel for an endoscope having excellent resistance to autoclave sterilization is known (see Patent Literature 1). The flexible channel for an endoscope described in Patent Literature 1 includes a spiral tube, a reticular tube that covers the spiral tube, and an outer cover that covers the outer periphery of the reticular tube. In this flexible channel for an endoscope, at least the outer surface of the outer cover contains a thermoplastic elastomer containing 0.5 to 50% by weight of a fullerene compound (see claim 1 in the same document).

CITATION LIST

Patent Literature

Patent Literature 1: JP 2006-116128 A

SUMMARY OF INVENTION

Technical Problem

The insertion portion of the endoscope using the flexible channel for an endoscope described in Patent Literature 1, various built-in objects such as an air supply tube, a water supply tube, an angle wire, a cable, an optical fiber, and so on are accommodated inside the flexible channel for an endoscope in which the spiral tube, the reticular tube, and the outer cover are layered.

The insertion portion has a complicated configuration because components or an adhesive agent for assembling the flexible channel for an endoscope and each built-in object is also required. Therefore, the assembly is time-consuming and expensive, and reprocessing such as cleaning after use is time-consuming.

According to one aspect, it is an object to provide an endoscope having an insertion portion with a simple configuration.

Solution to Problem

An endoscope includes an insertion portion, and an operation unit that is connected to one end of the insertion portion. The insertion portion includes a tube that is provided with a plurality of channels penetrating in a longitudinal direction, an operation unit that is connected to one end of the tube, and a distal tip that covers another end of the tube and has a through hole that smoothly communicates with a part of the plurality of channels.

Advantageous Effects of Invention

According to one aspect, it is possible to provide an endoscope having an insertion portion with a simple configuration.

BRIEF DESCRIPTION OF DRAWINGS

FIG. 7A is an enlarged cross-sectional view illustrating a first modification of the endoscope illustrated in FIGS. 1 and 2.

FIG. 7B is an enlarged perspective view illustrating the first modification of the endoscope illustrated in FIGS. 1 and 2.

FIG. 10A is an enlarged cross-sectional view illustrating a fourth modification of the endoscope illustrated in FIGS. 1 and 2.

FIG. 10B is an enlarged cross-sectional view illustrating the fourth modification of the endoscope illustrated in FIGS. 1 and 2.

FIG. 11 is an enlarged cross-sectional view illustrating a fifth modification of the endoscope illustrated in FIGS. 1 and 2.

DESCRIPTION OF EMBODIMENTS

Hereinafter, embodiments of the present disclosure will be described with reference to drawings. In the accompanying drawings, functionally identical elements may be represented by the same number. In the following description, "axial direction" indicates the axial direction of the insertion portion of the endoscope, "front side" indicates a subject side, and "rear side" indicates an operation unit side of the endoscope.

First Embodiment

<Configuration of Endoscope System>

Figure 1:
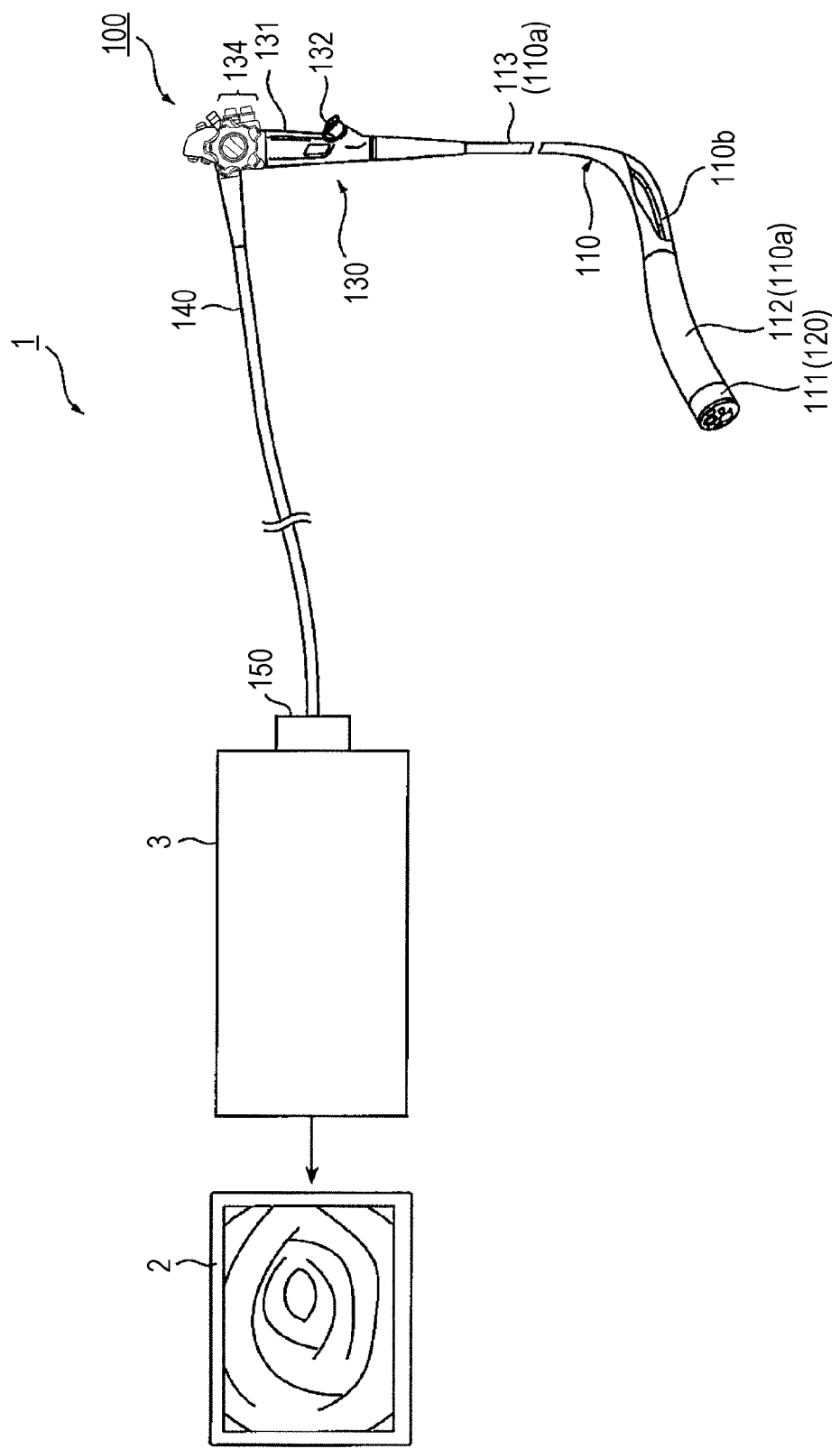
FIG. 1 is a schematic configuration diagram illustrating an endoscope system according to an embodiment of the present disclosure.

FIG. 1 is a schematic configuration diagram illustrating an endoscope system 1 according to this embodiment. In FIG. 1, connections between devices are indicated by arrows for the sake of simplicity of the drawing.

The endoscope system 1 of this embodiment includes, for example, a monitor 2, a processor 3, and an endoscope 100.

The endoscope 100 includes an insertion portion 110 that is inserted into a subject and an operation unit 130 that bends a part of the insertion portion 110. Although the details will be described later, in the endoscope 100 of this embodiment, at least a part of the insertion portion 110 is configured by a resin tube 110a. Further, the tube 110a has a plurality of resin channels 110b which form the tube 110a.

More specifically, the insertion portion 110 includes, for example, a distal tip 111 including an imaging unit 120, a bending section 112 that is bent by the operation unit 130, and a soft portion 113 between the bending section 112 and the operation unit 130. Then, at least a part of the bending section 112 and the soft portion 113 is configured by the tube 110a. The Shore A hardness of the resin forming the tube 110a is, for example, in a range of A30 or more and A95 or less in the case of polyurethane (urethane rubber), where a first portion is A30 and a second portion is A90. In this way, a plurality of different hardness can be adopted by changing the mixing ratio of materials.

A plurality of channels 110b of the tube 110a forming the insertion portion 110 of the endoscope 100 include, for example, a cable channel 36 (see FIG. 16) through which a signal cable for imaging is inserted. Further, the plurality of channels 110b of the tube 110a include, for example, a treatment tool channel 31 (see FIG. 16) for inserting a treatment tool such as forceps, and an air supply channel 32 (see FIG. 16) for performing air supply, and a water supply channel 33 (see FIG. 16) and an auxiliary water supply channel 34 (see FIG. 16) for water supply. Further, the plurality of channels 110b of the tube 110a may include, for example, an illumination channel through which a light guide fiber bundle for illumination is inserted.

Further, although not illustrated, the endoscope 100 includes, for example, a rigid member that is inserted into the channel 110b of the tube 110a that forms the insertion portion 110, and an angle wire 41 (see FIG. 15) that is inserted into the rigid member and connected to a bending mechanism of the bending section 112. As the rigid member, for example, a guide tube or a wire sheath 42 (see FIG. 15) configured by a metal closely wound coil or the like can be used. The operation unit 130 is provided so that the angle wire 41 can be operated. As the bending mechanism, for example, a known bending mechanism that bends the insertion portion of the known endoscope 100 can be applied.

The endoscope 100 also includes a connector cable 140 extending from the operation unit 130 and a connector unit 150 provided at an end portion of the connector cable 140. The connector unit 150 is connected to the processor 3. The processor 3 is a device for processing image data input from the endoscope 100 and generating a video signal. The monitor 2 is connected to the processor 3. The monitor 2 displays the internal image of the subject, which is captured by the endoscope 100 and generated by the processor 3.

<Endoscope>

Figure 2:
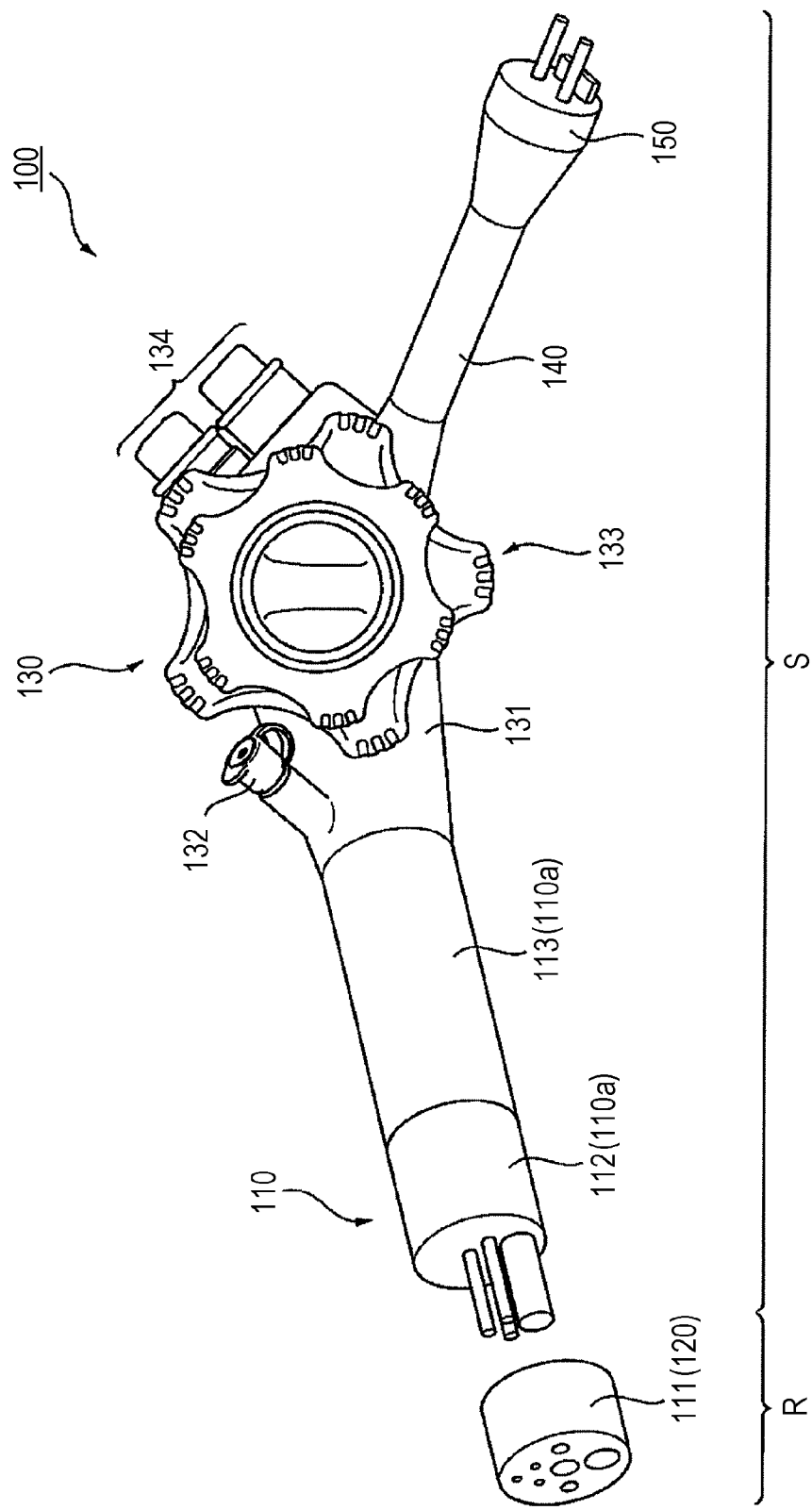
FIG. 2 is a schematic perspective view illustrating the overall configuration of the endoscope illustrated in FIG. 1.

FIG. 2 is a schematic perspective view illustrating the overall configuration of the endoscope 100 illustrated in FIG. 1. Hereinafter, the configuration of the endoscope 100 will be described in more detail with reference to FIG. 2. Note that the position and shape of the operation unit 130 in the endoscope 100 may differ from the actual position and shape for convenience of illustration.

As described above, the endoscope 100 includes the insertion portion 110 and the operation unit 130 that bends a part of the insertion portion 110. The insertion portion 110 includes, for example, the distal tip 111 including the imaging unit 120, the bending section 112 that is bent by the operation unit 130, and the soft portion 113 between the bending section 112 and the operation unit 130.

In the endoscope 100 of this embodiment, as described above, at least a part of the insertion portion 110 is configured by the resin tube 110a having the plurality of channels 110b, for example, a multi-lumen tube having pliability and flexibility. More specifically, at least a part of the bending section 112 and the soft portion 113 is configured by the resin tube 110a having the plurality of channels 110b, and the Shore A hardness of the resin constituting the tube 110a is, for example, A30 or more and A95 or less.

The Shore A hardness of the resin of the bending section 112 may be lower than the Shore A hardness of the resin of the soft portion 113, for example. Further, the length of the bending section 112 and the length of the insertion portion 110 including the bending section 112 and the soft portion 113 can be set to a length according to the application of the endoscope 100. For example, in the case of the upper digestive tract, the length of the bending section 112 and the length of the insertion portion 110 are about 40 mm to 60 mm and about 1000 mm to 1100 mm, respectively. In the case of the large intestine, the length of the bending section 112 and the length of the insertion portion 110 are about 80 mm to 100 mm and about 1100 mm to 1700 mm, respectively. In the case of the duodenum, the length of the bending section 112 and the length of the insertion portion 110 are about 30 mm to 40 mm and 1200 mm to 1300 mm, respectively.

In the example illustrated in FIGS. 1 and 2, the distal tip 111 of the insertion portion 110 is configured by the imaging unit 120. However, the distal tip 111 of the insertion portion 110 may be configured by the tube 110*a*, and the imaging unit 120 may be arranged inside the tube 110*a* of the distal tip 111.

In addition, the endoscope 100 of this embodiment is, for example, a single-use endoscope including a single-use portion S and a reusable portion R. The single-use portion S includes, for example, the tube 110*a* that forms at least a part of the insertion portion 110, and is replaced each time the endoscope 100 is used. The reusable portion R includes, for example, the imaging unit 120, is collected for each single use of the endoscope 100, is cleaned and sterilized, and is reused.

The single-use portion S may be only the tube 110*a* forming the insertion portion 110, but may be the entire insertion portion 110 including the tube 110*a*, or may be a part of the insertion portion 110 including the tube 110*a*. Further, the single-use portion S may include the operation unit 130, the connector cable 140, and the connector unit 150. Further, the bending section 112 may be configured by the one tube 110*a* integrally with the soft portion 113, but may be configured by the tube 110*a* forming the soft portion 113 and another tube 110*a*. Each part of the single-use portion S is preferably made of resin as much as possible from the viewpoint of cost reduction.

The reusable portion R may be only the imaging unit 120, but may also include a part of the insertion portion 110 excluding the tube 110*a*. For example, the reusable portion R may include the bending section 112. In addition, the reusable portion R may include a part or all of the operation unit 130, the connector cable 140, and the connector unit 150.

The resin forming the tube 110*a* may be a non-porous resin as a whole, that is, a solid resin that is not a porous resin, or at least a part thereof may be a porous resin. The tube 110*a* can be manufactured by extrusion molding of a resin material, for example.

As a resin forming the tube 110*a*, for example, PTFE (Polytetrafluoroethylene), ePTFE (expanded PTFE), PE (Polyethylene), HDPE (High Density Polyethylene), PP (Polypropylene), or the like can be used. As a non-porous resin forming the tube 110*a*, for example, PU (Polyurethane), PP (Polypropylene), PE (Polyethylene), Polyamide (Polyamide), or the like can be used.

The Shore A hardness of the resin forming the tube 110*a* can be in a range of A30 to A95, for example. The Shore A hardness of the resin can be adjusted within the above range by changing the mixing ratio of the materials. For example, the mixing ratio of the resin material forming the tube 110*a* may be changed in the vicinity of the boundary between the bending section 112 and the soft portion 113, so that the Shore A hardness of the bending section 112 and the Shore A hardness of the soft portion 113 can be made different.

More specifically, the Shore A hardness of the resin in the bending section 112 can be, for example, the softest A30. The Shore A hardness of the resin in the soft portion 113 is higher than the Shore A hardness of the resin in the bending section 112, for example, in a range of A40 or more and A70 or less, or a range of A45 or more and A70 or less. Further, the Shore A hardness of the resin in the soft portion 113 can be set according to the outer diameter of the tube 110*a* forming the soft portion 113, for example, as illustrated in Table 1 below. Here, the material of the resin is PU. Thereby, the pliability and flexibility of the bending section 112 can be improved, and the bending section 112 can have flexural rigidity suitable for bending operation.

TABLE 1

| Outer diameter of tube | Shore A hardness of resin |
| --- | --- |
| φ10 mm or less | A60 or more, A70 or less |
| φ10 mm or more, φ12 mm or less | A50 or more, A60 or less |
| φ12 mm or more, φ14 mm or less | A40 or more, A50 or less |

The tube 110*a* forming the insertion portion 110 may be in a state of being constantly compressed in the axial direction between the imaging unit 120 and the operation unit 130, for example. As a result, the density of the tubes 110*a* can be improved, and the flexural rigidity of the insertion portion 110 can be improved.

Further, in the tube 110*a* forming the insertion portion 110, the Shore A hardness of the resin may change in the axial direction or the radial direction of the tube 110*a*. For example, in the tube 110*a* forming the insertion portion 110, the Shore A hardness of the resin may change in the radial direction of the tube 110*a*. More specifically, the Shore A hardness of the outer surface of the tube 110*a* may be higher than the Shore A hardness of the center of the tube 110*a* in the radial direction of the tube 110*a*.

Further, in the radial direction of the tube 110*a*, the Shore A hardness may be reduced continuously or stepwise from the center toward the outer surface. In addition, in the radial direction of the tube 110*a*, the Shore A hardness may be reduced continuously or stepwise from the outer surface toward the center. The stepwise change in Shore A hardness includes a discontinuous change in Shore A hardness. Here, the discontinuous change in Shore A hardness includes that a portion having a constant Shore A hardness is between the portions having a changing Shore A hardness, or that the Shore A hardness changes stepwise.

Further, the tube 110*a* may have a non-porous resin layer having a porosity of 0% on the outer surface on the radially outer side and a portion in the vicinity thereof. Thereby, it is possible to prevent the liquid from permeating from the outer surface of the insertion portion 110. Further, the tube 110*a* may have a non-porous resin layer having a porosity of 0% on the inner wall surface of the channel 110*b* and a portion in the vicinity thereof. Thereby, it is possible to prevent the liquid from permeating from the inner wall surface of the channel 110*b* of the insertion portion 110.

Further, the Shore A hardness of the resin forming the tube 110*a* is continuously or stepwise changed in the axial direction of the tube 110*a* from the end portion on the operation unit 130 side, which is the proximal end of the insertion portion 110, toward the distal tip 111 of the insertion portion 110. For example, as described above, the Shore A hardness of the resin of the bending section 112 may be lower than the Shore A hardness of the resin of the soft portion 113 in the axial direction of the tube 110a.

The stepwise change in Shore A hardness in the axial direction includes a discontinuous change in Shore A hardness, as in the case of the radial direction. Here, the discontinuous change in Shore A hardness includes that a portion having a constant Shore A hardness is between the portions having a changing Shore A hardness, or that the Shore A hardness changes stepwise. Further, the material of the tube 110a in the portion of the insertion portion 110 connected to the operation unit 130 may be, for example, a non-porous resin having a porosity of 0%.

FIGS. 3A to 3E are graphs illustrating examples of flexural rigidity of the tube 110a forming the insertion portion 110 illustrated in FIG. 2. FIG. 3F is a graph illustrating an example of flexural rigidity of the insertion portion 110 illustrated in FIG. 2. In the graphs illustrated in FIGS. 3A to 3F, the vertical axis represents the flexural rigidity of the tube 110a or the insertion portion 110, and the horizontal axis represents the distance from the distal tip of the insertion portion 110.

Figure 3A:
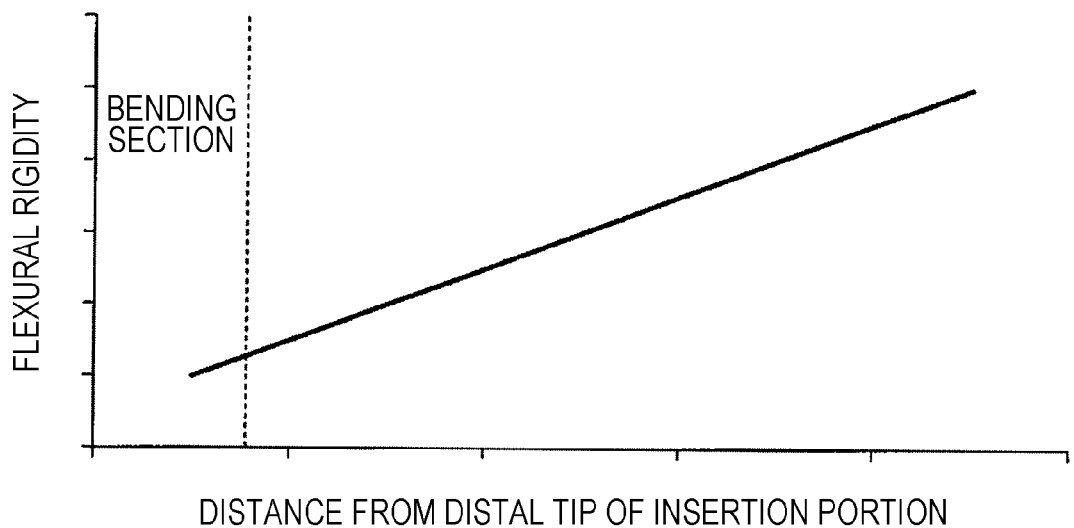
FIG. 3A is a graph illustrating an example of flexural rigidity of a tube forming an insertion portion illustrated in FIG. 2.

In the example illustrated in FIG. 3A, the Shore A hardness of the resin of the tube 110a is continuously increased at a substantially constant rate from the distal tip where the bending section 112 is provided to the proximal end connected to the operation unit 130. As a result, the flexural rigidity of each tube 110a that forms the insertion portion 110 increases from the distal tip to the proximal end at a substantially constant rate.

Further, as described above, when the guide tube for inserting the angle wire 41 is inserted into the channel 110b of the tube 110a forming the insertion portion 110, the guide tube may have higher flexural rigidity than the tube 110a. In this case, the guide tube may be inserted into the channel 110b of the tube 110a on the proximal end side of the insertion portion 110 rather than the bending section 112, that is, on the operation unit 130 side rather than the bending section 112.

Figure 3B:
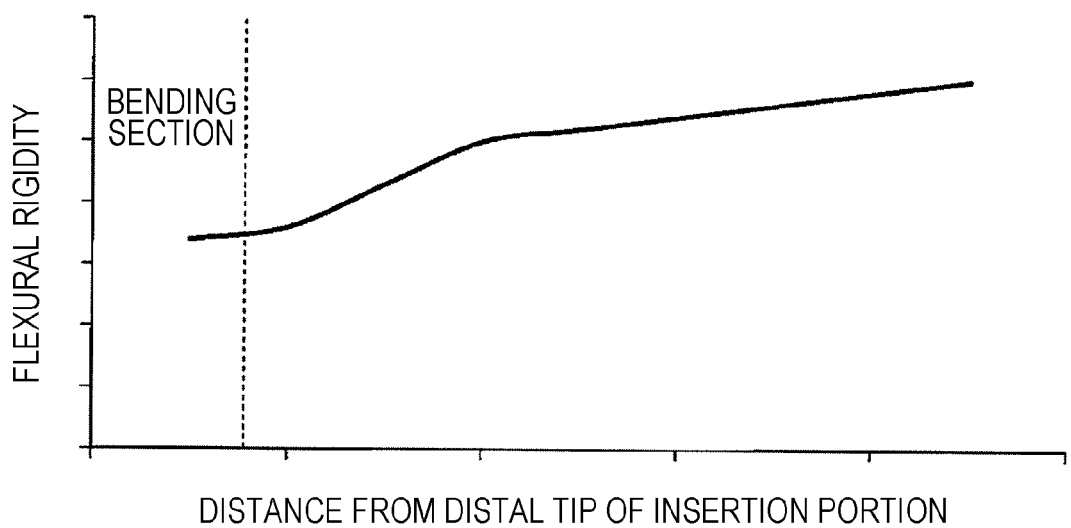
FIG. 3B is a graph illustrating an example of flexural rigidity of the tube forming the insertion portion illustrated in FIG. 2.

In the example illustrated in FIG. 3B, in the tube 110a, the Shore A hardness of the resin continuously increases at a substantially constant rate from the distal tip to the proximal end as in the example illustrated in FIG. 3A, but four guide tubes are inserted into the channel 110b in the soft portion 113 on the proximal end side of the insertion portion 110 rather than the bending section 112. The flexural rigidity of the guide tube is higher than the flexural rigidity of the tube 110a. Therefore, in the example illustrated in FIG. 3B, the flexural rigidity of the tube 110a is higher in the portion of the insertion portion 110 on the proximal end side rather than the bending section 112, as compared with the example illustrated in FIG. 3A.

As the guide tube, for example, a hard tube made of fluororesin (PTFE, FPA, FEP, etc.) or polyimide can be used. In addition to the guide tube, a rigid member having higher flexural rigidity than the tube 110a may be inserted into the channel 110b of the tube 110a for the purpose of improving the flexural rigidity of the tube 110a. As a rigid member, for example, a close contact coil (stay coil) made of metal such as a spring stainless material (SUS304-WPB) can be used. Such a hard tube or a metal contact coil can be inserted into the channel 110b for inserting the angle wire 41 of the tube 110a over the entire length of the soft portion 113.

Figure 3C:
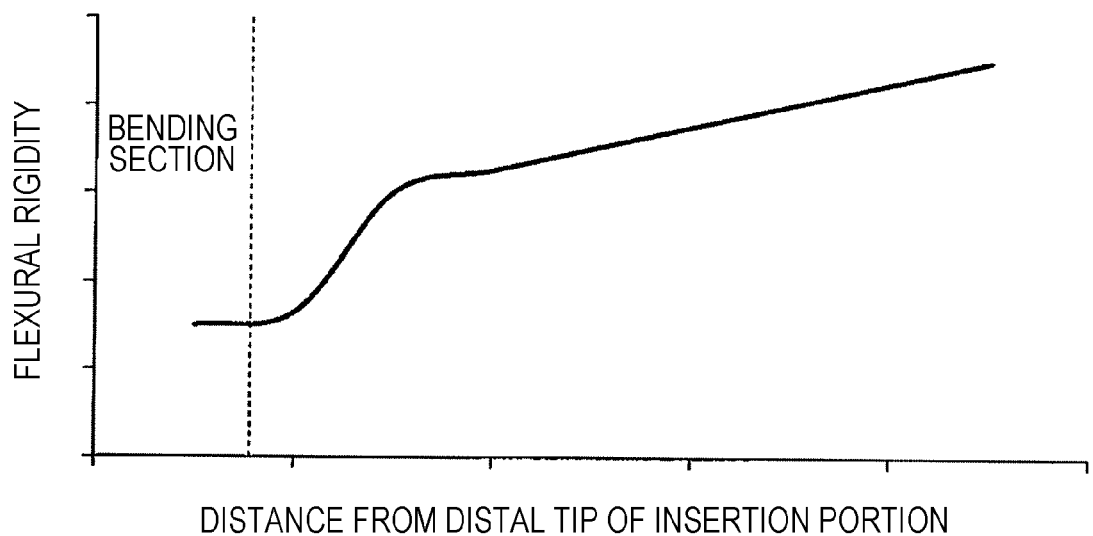
FIG. 3C is a graph illustrating an example of flexural rigidity of the tube forming the insertion portion illustrated in FIG. 2.

In the example illustrated in FIG. 3C, in the tube 110a, the Shore A hardness of the resin is set to a relatively low constant value on the distal tip 111 side where the bending section 112 is provided, and is continuously increased from the distal tip side to the proximal end side in the soft portion 113 on the proximal end side rather than the bending section 112. As a result, the flexural rigidity of each tube 110a becomes a relatively low constant value in the bending section 112, and continuously increases from the distal tip side to the proximal end side in the soft portion 113 on the proximal end side rather than the bending section 112.

Figure 3D:
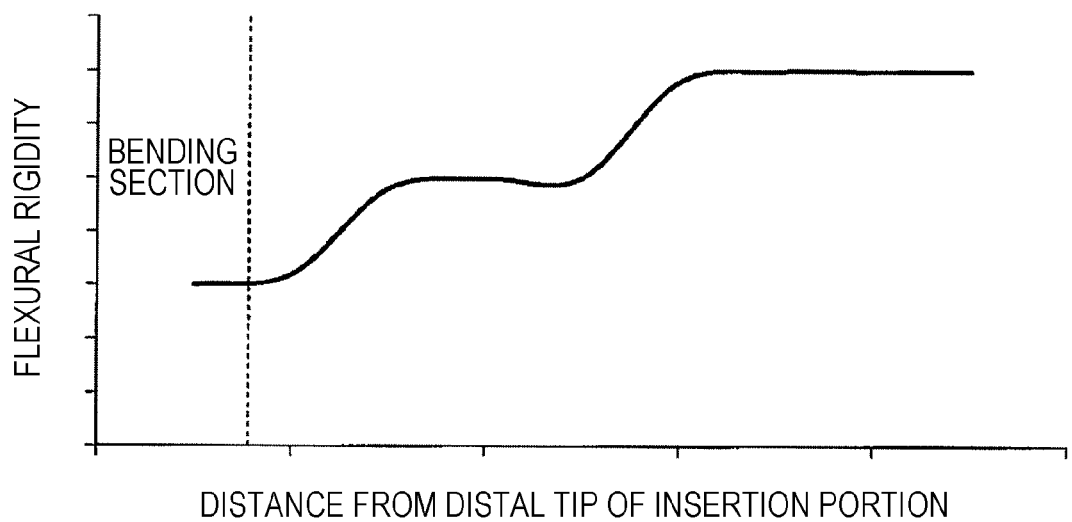
FIG. 3D is a graph illustrating an example of flexural rigidity of the tube forming the insertion portion illustrated in FIG. 2.

In the example illustrated in FIG. 3D, in the tube 110a, the Shore A hardness of the resin gradually increases in two steps from the distal tip to the proximal end. As a result, the flexural rigidity of each tube 110a that forms the insertion portion 110 gradually increases in two steps from the distal tip to the proximal end. The Shore A hardness of the resin forming the tube 110a may be increased stepwise from the distal tip to the proximal end in three or more steps, or may stay in one step between the bending section 112 and the soft portion 113.

In the example illustrated in FIG. 3D, the portion having the lowest flexural rigidity including the bending section 112 is a pliable portion, the portion having the highest flexural rigidity of the insertion portion 110 on the operation unit 130 side is a hard portion, and the portion having a constant flexural rigidity between the hard portion and the soft portion is defined as a middle portion. In this case, the Shore A hardness of the resin forming the tube 110a can be set according to the outer diameter of the tube 110a forming the soft portion 113, for example, as illustrated in Table 2 below. The Shore A hardness of the pliable portion is A30 regardless of the outer diameter of the tube 110a, for example. The length of the pliable portion is, for example, about 400 mm.

TABLE 2

| Outer diameter | Shore A hardness of resin | |
|---|---|---|
| of tube | Middle portion | Hard portion |
| φ10 mm or less | A30 or more, A45 or less | A60 or more, A70 or less |
| φ10 mm or more, φ12 mm or less | A30 or more, A40 or less | A55 or more, A65 or less |
| φ12 mm or more, φ14 mm or less | A30 or more, A35 or less | A45 or more, A55 or less |

The soft portion 113 of the endoscope 100 is required to transmit the operation at hand to the distal tip of the insertion portion 110. Specifically, it is important that an operation at hand, such as twisting or pushing and pulling, is directly transmitted to the distal tip of the insertion portion 110 in a state where the soft portion 113 is looped in the large intestine. Further, it is also important that a repulsive force from a mucous membrane at the distal tip of the insertion portion 110 is transmitted to the fingers of the operator who grips the soft portion 113 when inserting the insertion portion 110 into the subject, from the viewpoint of preventing perforation and the like.

Further, in the case of the endoscope 100 for the large intestine, it is difficult to insert the insertion portion 110 into the sigmoid colon, the spleen curve, and the liver curve. Therefore, for example, the length of the pliable portion is set to about 400 mm, and the Shore A hardness of the resin forming the tube 110a is changed stepwise according to the outer diameter as described above, whereby the insertion into the sigmoid colon, spleen curve, and liver curve becomes easy. Moreover, the operation at hand is easily transmitted to the distal tip, and the repulsive force from the subject is easily transmitted to the operator's finger. The Shore A hardness of the hard portion may be continuously increased toward the operation unit 130 side.

Figure 3E:
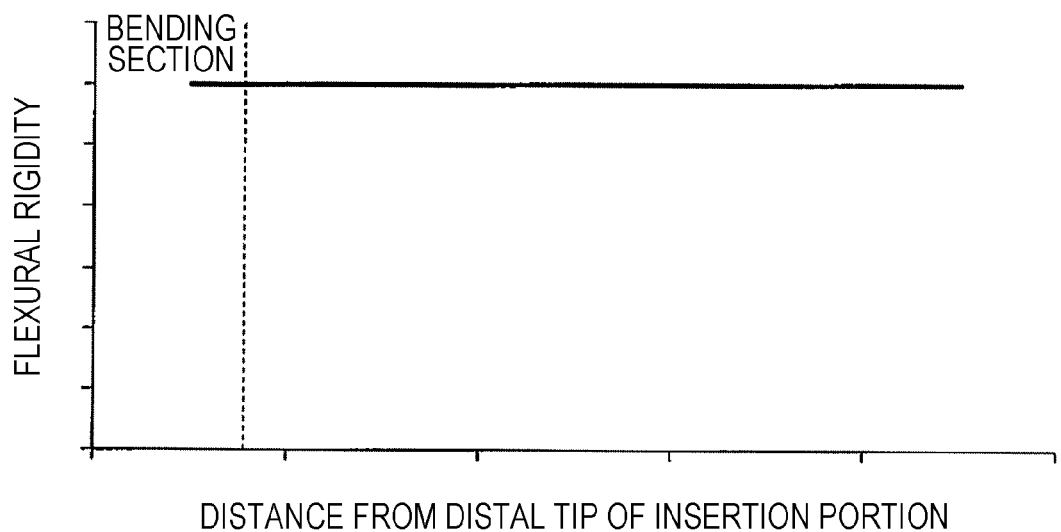
FIG. 3E is a graph illustrating an example of flexural rigidity of a tube forming the insertion portion illustrated in FIG. 2.
Figure 3F:
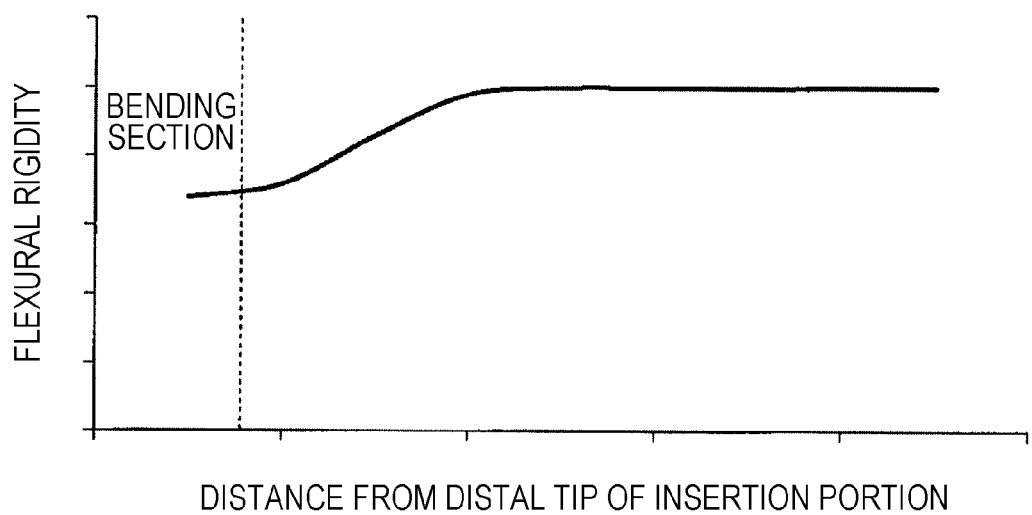
FIG. 3F is a graph illustrating an example of flexural rigidity of the insertion portion illustrated in FIG. 2.

In the example illustrated in FIG. 3E, the tube 110a has a constant Shore A hardness of the resin from the distal tip to the proximal end. Therefore, the flexural rigidity of each tube 110a that forms the insertion portion 110 is constant from the distal tip to the proximal end.

In the example illustrated in FIG. 3F, the tube 110a has a constant Shore A hardness of the resin from the distal tip to the proximal end as in the example illustrated in FIG. 3E, and the guide tube of the angle wire 41 is inserted into the channel 110b as in the example illustrated in FIG. 3B. Further, in the example illustrated in FIG. 3F, in addition to the guide tube, other members forming the insertion portion 110 are inserted and arranged in the channel 110b to form the insertion portion 110. Therefore, in the example illustrated in FIG. 3F, the flexural rigidity of the tube 110a is higher in the portion of the insertion portion 110 on the proximal end side rather than the bending section 112, as compared with the example illustrated in FIG. 3E.

Figure 4:
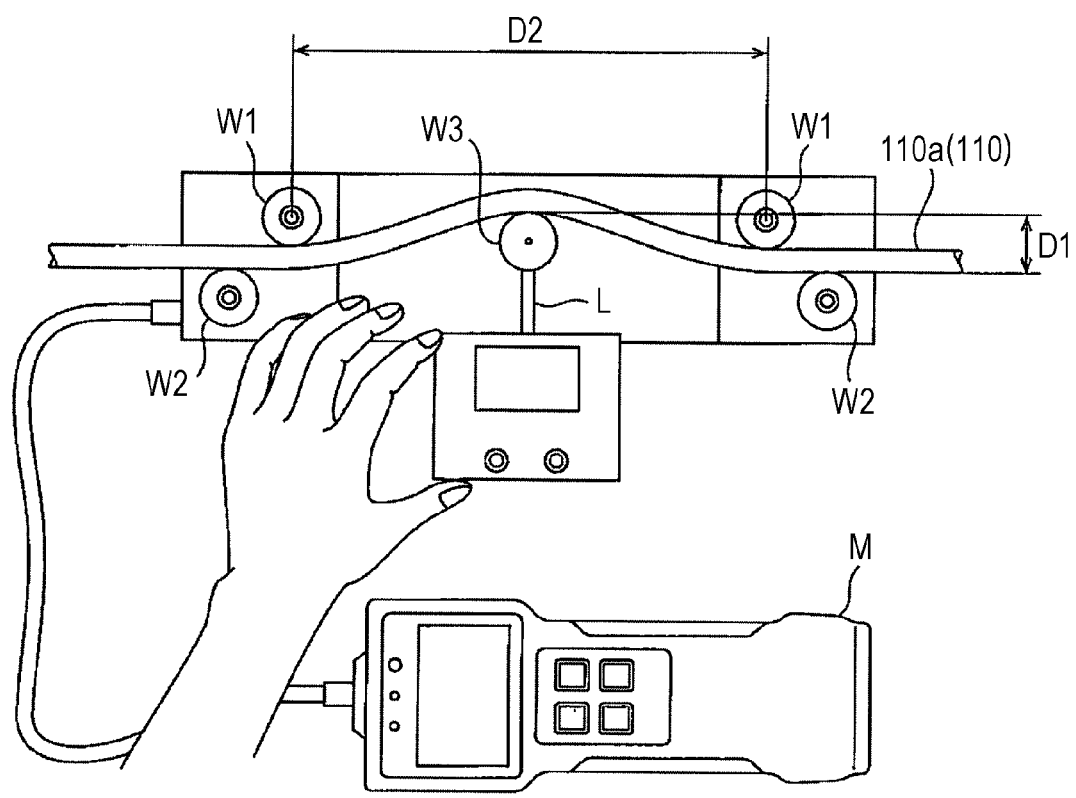
FIG. 4 is a diagram illustrating an example of a method for measuring flexural rigidity.

FIG. 4 is a diagram illustrating an example of a method of measuring flexural rigidity. The flexural rigidity of each tube 110a that forms the insertion portion 110, the rigid member inserted into the tube 110a and its channel 110b, or the insertion portion 110 forming the tube 110a, and other members can be measured by the following procedure, for example. First, the tube 110a is arranged between two pairs of rollers W1 and W2 while being straightened. As a result, the tube 110a is in a state of being supported from both sides in the radial direction by the two pairs of rollers W1 and W2 that are separated in the axial direction.

Next, in the middle of the two pairs of rollers W1 and W2 in the axial direction of the tube 110a, a measuring rod L of a measuring instrument M in the radial direction of the tube 110a presses a roller W3 arranged on one side in the radial direction of the tube 110a by a predetermined amount D1 of indentation in the radial direction of the tube 110a, and the tube 110a supported between the two pairs of rollers W1 and W2 is bent. In this state, the reaction force acting on the measuring rod L is measured by the measuring instrument M, and this reaction force is used as the flexural rigidity of each tube 110a or the insertion portion 110. For example, when the outer diameter of the tube 110a is φ8 mm, the distance D2 between the rollers W1 separated in the axial direction of the tube 110a can be set to 200 mm and the amount D1 of indentation can be set to 20 mm.

As illustrated in FIG. 2, the operation unit 130 of the endoscope 100 includes an operation unit body 131 that forms a grip section, and a treatment tool inlet 132 provided on the insertion portion 110 side of the operation unit body 131. The treatment tool inlet 132 is an opening provided in the operation unit 130 and communicates with the treatment tool channel 31 described above. Further, the operation unit body 131 is provided with a bending operation knob 133 for operating the bending of the bending section 112, switches 134 related to each operation of the endoscope 100, and the like. The proximal end portion of the tube 110a forming the insertion portion 110 is connected to, for example, the operation unit body 131.

Figure 5:
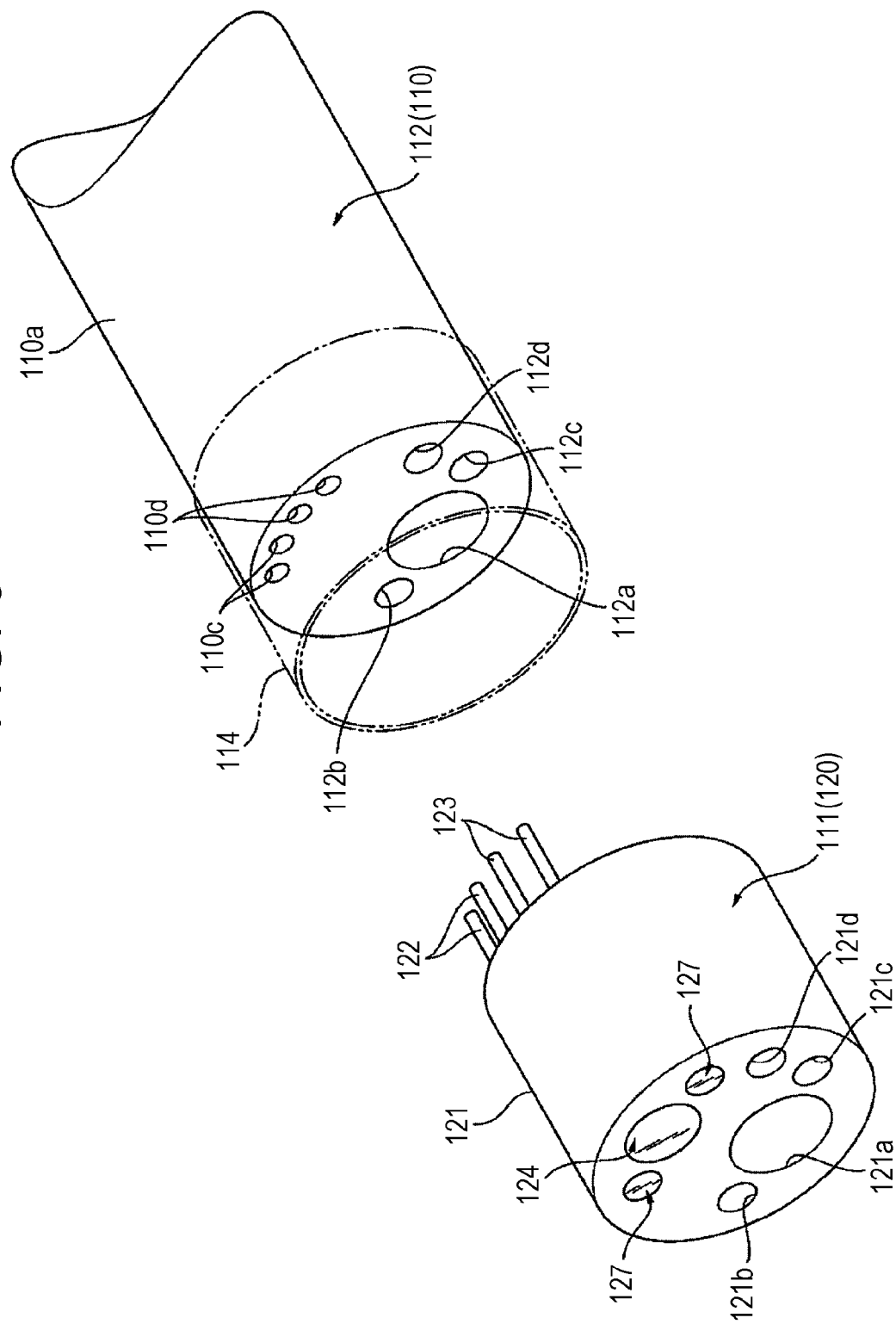
FIG. 5 is an enlarged view illustrating an example of an imaging unit of the endoscope illustrated in FIGS. 1 and 2.

FIG. 5 is an enlarged view illustrating an example of the imaging unit 120 of the endoscope 100 illustrated in FIGS. 1 and 2. In the example illustrated in FIG. 5, the insertion portion 110 includes an opening 112a of the treatment tool channel 31, an opening 112b of the air supply channel 32, and an opening 112c of the water supply channel 33, and an opening 112d of the auxiliary water supply channel 34 at the distal tip of the bending section 112 formed by the tube 110a.

The insertion portion 110 also includes a contact-type power source connector 110c and a signal connector 110d at the distal tip of the tube 110a. The power source connector 110c is connected to the power source terminal of the connector unit 150, for example, via a power source cable passed through the cable channel 36 of the tube 110a. The signal connector 110d is connected to the signal terminal of the connector unit 150, for example, via a signal cable that passes through the cable channel 36 of the tube 110a that forms the insertion portion 110.

The imaging unit 120 includes, for example, a cylindrical body portion 121, a forceps port 121a provided in the body portion 121, an air supply port 121b, a water supply port 121c, and an auxiliary water supply port 121d. The forceps port 121a, the air supply port 121b, the water supply port 121c, and the auxiliary water supply port 121d are openings of the treatment tool channel, the air supply channel, the water supply channel, and the auxiliary water supply channel provided in the body portion 121, respectively, and communicate with the treatment tool channel 31, the air supply channel 32, the water supply channel 33, and the auxiliary water supply channel 34 provided in the tube 110a via the openings 112a, 112b, 112c, and 112d of the tube 110a. Further, the imaging unit 120 has a power source pin 122 and a signal pin 123 at the rear end of the body portion 121 connected to the distal tip of the tube 110a.

The joint between the imaging unit 120 and the insertion portion 110 is covered with a fractured portion 114 of a tube shape. As a material of the fractured portion 114, for example, a resin having pliability and flexibility can be used, as with the tube 110a forming the insertion portion 110. The fractured portion 114 covers not only the joint between the imaging unit 120 and the insertion portion 110 but also, for example, the rear end of the imaging unit 120 adjacent to the joint and the distal tip of the bending section 112. The fractured portion 114 is, for example, adhered or joined to the rear end of the imaging unit 120 and the distal tip of the bending section 112, and is broken when the imaging unit 120 forming the distal tip 111 of the insertion portion 110 is removed from the insertion portion 110.

Figure 6:
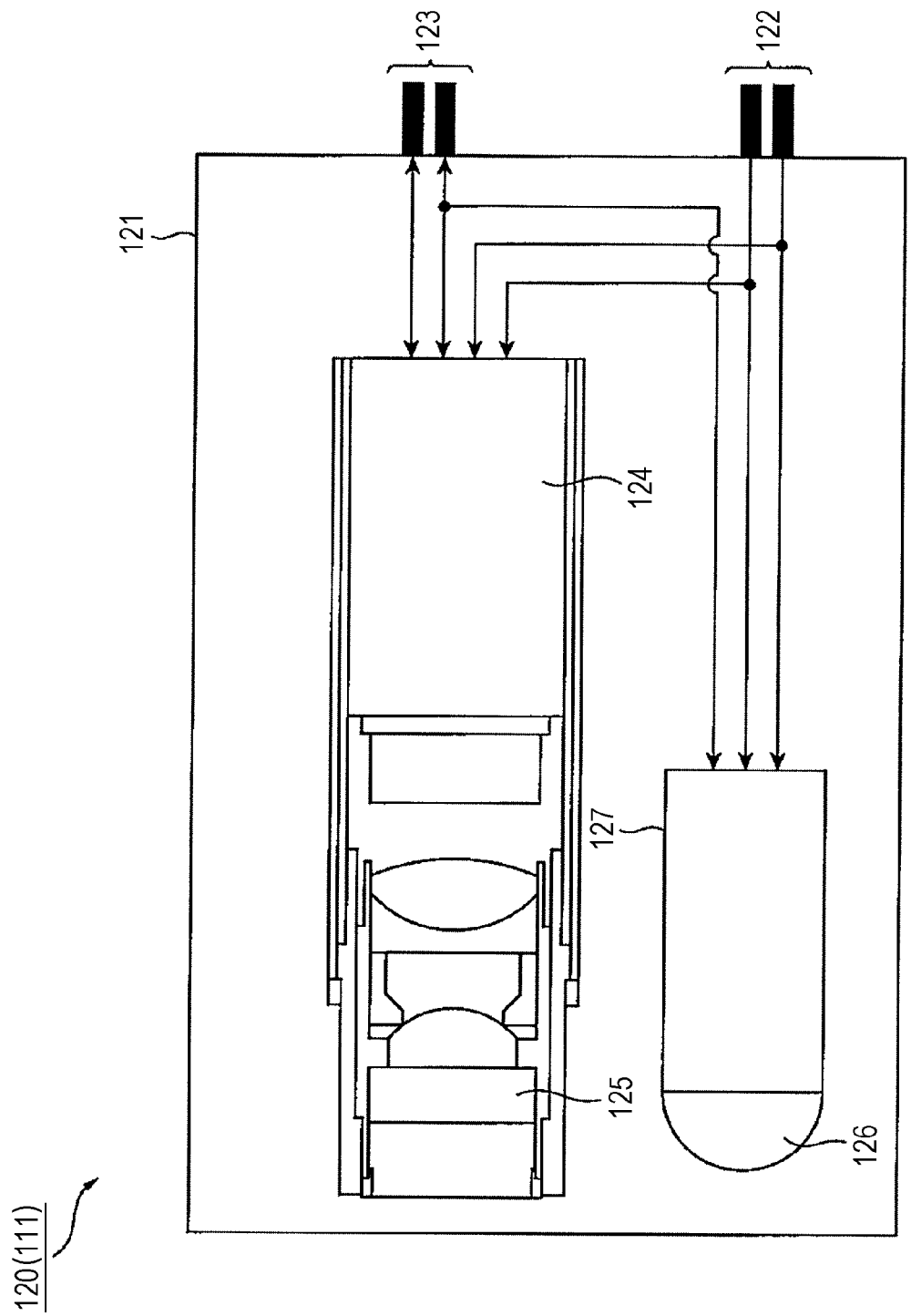
FIG. 6 is a schematic cross-sectional view illustrating an example of the configuration of the imaging unit illustrated in FIG. 5.

FIG. 6 is a schematic cross-sectional view illustrating an example of the configuration of the imaging unit 120 illustrated in FIG. 5. The imaging unit 120 includes at least an image sensor 124 such as CMOS or CCD. In this embodiment, the imaging unit 120 includes, for example, an image sensor 124, an objective lens 125, and a small LED (Light Emitting Diode) illumination 127 including a lens 126. The body portion 121 hermetically closes and seals each part of the imaging unit 120 including the image sensor 124, for example. The imaging unit 120 includes the power source pin 122 and the signal pin 123 at the rear end of the body portion 121. Note that the imaging unit 120 does not have to include all the components illustrated in FIG. 6, and may include, for example, the minimum number of components that enable reuse of the image sensor 124.

The power source pin 122 is connected to, for example, the image sensor 124 and the small LED illumination 127. By inserting and connecting the power source pin 122 into the power source connector 110c at the distal tip of the tube 110a, it becomes possible to supply power to the image sensor 124 and the small LED illumination 127. The signal pin 123 is connected to, for example, the image sensor 124 and the small LED illumination 127. By inserting and connecting the signal pin 123 into the signal connector 110d at the distal tip of the tube 110a, the image signal of the image sensor 124 can be output to the signal terminal of the connector unit 150 via the signal cable. Note that the connection for outputting the image signal of the image sensor 124 is not limited to the contact type using the pins and the connector, and may be changed to a wireless type connection such as Bluetooth (registered trademark), for example.

The body portion 121 is made of, for example, a hard resin different from the pliable resin that forms the tube 110a. The body portion 121 may be partially or wholly transparent, for example. In this case, lenses such as the objective lens 125 and the illumination lens 126 may be integrally formed with the body portion 121. When the imaging unit 120 is configured by the image sensor 124 alone, the imaging unit 120 does not need to include the main body portion 121. In this case, the imaging unit 120 is configured by the image sensor 124 sealed with resin or the like, and can be arranged so as to be embedded at the distal tip of the tube 110a that forms the distal tip 111 of the insertion portion 110.

Hereinafter, the operation of the endoscope 100 of this embodiment will be described.

As described above, the endoscope 100 of this embodiment includes the insertion portion 110 including the imaging unit 120, and the operation unit 130 that bends a part of the insertion portion 110. Then, at least a part of the insertion portion 110 is configured by a resin tube 110a. Further, the tube 110a has a plurality of resin channels 110b which form the tube 110a.

As described above, by configuring at least a part of the insertion portion 110 of the endoscope 100 with the resin tube 110a, the insertion portion 110 may have the pliability, flexibility, and smoothness of the outer surface of the tube 110a. Therefore, it is possible to prevent deterioration of operability and insertability when the insertion portion 110 is inserted into the body of a patient. Further, the tube 110a has the plurality of resin channels 110b forming the tube 110a itself, that is, the resin tube 110a having the plurality of channels 110b, for example, a multi-lumen tube. As a result, the insertion portion 110 can be easily manufactured with a relatively inexpensive material, and the cost of the endoscope 100 can be reduced.

Further, the endoscope 100 of this embodiment includes the insertion portion 110 and the operation unit 130 that bends a part of the insertion portion 110, as described above. The insertion portion 110 includes the distal tip 111 including the imaging unit 120, the bending section 112 that is bent by the operation unit 130, and the soft portion 113 between the bending section 112 and the operation unit 130. Further, at least a part of the bending section 112 and the soft portion 113 is configured by the resin tube 110a having the plurality of channels 110b. The Shore A hardness of the resin forming the tube 110a is A30 or more and A95 or less.

As described above, by configuring at least a part of the bending section 112 and the soft portion 113 by the resin tube 110a, the insertion portion 110 may have the pliability, flexibility, and smoothness of the outer surface of the tube 110a. Therefore, it is possible to prevent deterioration in operability and insertability when the bending section 112 and the soft portion 113 are inserted into the patient's body. Further, since the Shore A hardness of the resin forming the tube 110a is A30 or more and A95 or less, the flexural rigidity corresponding to the Shore A hardness of the tube 110a can be imparted to the bending section 112 and the soft portion 113.

For example, when the Shore A hardness of the resin of the bending section 112 is lower than the Shore A hardness of the resin of the soft portion 113, the flexural rigidity of the tube 110a in the bending section 112 can be lowered than the flexural rigidity of the tube 110a in the soft portion 113. As a result, the operation of bending the bending section 112 is facilitated, and the operability of the endoscope 100 can be further improved.

Further, the endoscope 100 of this embodiment includes the single-use portion S including a tube 110a that is replaced for each use, and the reusable portion R including the imaging unit 120 that is collected and reused for each use. As a result, the single-use portion S including the relatively inexpensive tube 110a can be made disposable, and an endoscopic examination can be performed while always maintaining a high level of cleanliness.

Further, by replacing the single-use portion S including the tube 110a with a new one after each use and disposing of the single-use portion S, it is possible to save the labor such as cleaning, sterilization, and sanitization of the insertion portion 110. The risk of temporal damage and failure of the insertion portion 110 can be reduced. In addition, the reusable portion R including the relatively expensive imaging unit 120 is recovered for each use, washed, sterilized, and sanitized to be reused, so that the maintenance cost of the single-use endoscope 100 in which the parts other than the reusable portion R are disposable can be reduced.

In addition, in the endoscope 100 of this embodiment, the insertion portion 110 includes the fractured portion 114 that is fractured when the imaging unit 120 is removed. Thus, for example, after the use of the endoscope 100, if a third party who does not have the authority to exchange the single-use portion S removes the imaging unit 120, the fractured portion 114 breaks and the endoscope 100 becomes impossible to be reconfigured. Therefore, it is possible to prevent the reuse of the single-use portion S including the tube 110a and the unauthorized removal of the imaging unit 120. Therefore, it is possible to improve the traceability of the endoscope 100 and further improve the safety and reliability.

Note that, as described above, when the imaging unit 120 is embedded in the distal tip of the tube 110a forming the distal tip 111 of the insertion portion 110, the tube 110a serves as the fractured portion 114. That is, in order to collect the reusable portion R including the imaging unit 120, it is necessary to break the tube 110a and take out the imaging unit 120 in the tube 110a.

Thus, after the use of the endoscope 100, if a third party who does not have the authority to exchange the single-use portion S removes the imaging unit 120, the tube 110a is broken and the endoscope 100 becomes impossible to be reconfigured. Therefore, it is possible to prevent the reuse of the single-use portion S including the tube 110a and the unauthorized removal of the imaging unit 120. Therefore, it is possible to improve the traceability of the endoscope 100 and further improve the safety and reliability.

Therefore, according to the endoscope 100 of this embodiment, removal of the imaging unit 120 by an unauthorized third party can be prevented by the fractured portion 114 or the tube 110a. Even if the imaging unit 120 is removed, the fractured portion 114 or the tube 110a is broken, so that it is possible to easily determine that the imaging unit 120 has been removed.

On the other hand, when the authorized administrator who manages the endoscope 100 collects the reusable portion R including the imaging unit 120, the fractured portion 114 or the tube 110a is broken, and the imaging unit 120 and the small LED illumination 127 can be easily taken out. Then, the reusable portion R including the taken-out imaging unit 120 can be washed and sterilized, and these can be reused.

The image sensor 124 and the small LED illumination 127 of the imaging unit 120 have the same performance as the image sensor and the small LED illumination used in the imaging unit of a normal reuse endoscope. Since the imaging unit 120 including such a high-performance image sensor 124 and the small LED illumination 127 is expensive, after the used endoscope 100 is collected from the user, it is removed by the administrator of the endoscope 100, washed, sterilized, sanitized, and supplied for reuse.

The inexpensive single-use portion S including the tube 110a is discarded and incinerated, for example. The resin forming the single-use portion S may be reused as a raw material after being dissolved, for example. That is, a new endoscope 100 is manufactured by the reusable portion R including the cleaned, sterilized, and sanitized imaging unit 120 and the single-use portion S including the completely new tube 110a, and is supplied to the user again.

Further, when at least a part of the tube 110a is made of a porous resin, the pliability and flexibility of the porous resin portion can be improved more than the pliability and flexibility of the non-porous portion which is not made of porous resin. Therefore, the operability and insertability of the insertion portion 110 can be improved.

Further, as described above, the Shore A hardness of the resin may change in the axial direction or the radial direction of the tube 110a. As the Shore A hardness of the resin decreases, the pliability and flexibility of the resin improve. On the other hand, when the Shore A hardness of the resin increases, the pliability and flexibility of the resin decrease.

Therefore, for example, the pliability and flexibility can be changed by changing the Shore A hardness of the resin forming the tube 110a in the axial direction, that is, the longitudinal direction of the insertion portion 110. Further, the pliability and flexibility of the insertion portion 110 can be improved by changing the Shore A hardness of the resin forming the tube 110a in the radial direction of the insertion portion 110.

Specifically, for example, the Shore A hardness of the resin forming the tube 110a can be increased from the radially inner side to the outer side of the insertion portion 110, or the Shore A hardness of the resin forming the tube 110a can be increased from the radially outer side to the inner side of the insertion portion 110.

Further, the endoscope 100 of this embodiment includes, as described above, the rigid member inserted into the channel 110b of the tube 110a, and the angle wire 41 which is inserted into the rigid member and connected to the bending mechanism of the bending section 112. Then, the operation unit 130 is provided so that the angle wire 41 can be operated. Accordingly, the angle wire 41 can be operated by the operation unit 130, and the bending mechanism can be bent by the angle wire 41. Therefore, the bending section 112 can be freely bent by operating the operation unit 130.

Further, the rigid member inserted into the channel 110b of the tube 110a has, for example, a higher flexural rigidity than the tube 110a, and is inserted into the channel 110b in the soft portion 113 on the proximal end side rather than the bending section 112. With this rigid member, the channel 110b can be protected by the soft portion 113 on the proximal end side rather than the bending section 112, and the channel 110b can be prevented from being damaged by the guide wire. Further, the flexural rigidity of the soft portion 113 can be improved by the rigid member inserted into the channel 110b of the tube 110a, and the operability and insertability when inserting the insertion portion 110 into the patient's body can be improved.

As described above, according to this embodiment, it is possible to provide the endoscope 100 and the endoscope system 1 capable of suppressing the cost without deteriorating the operability and the insertability.

<First Modification of Endoscope>

FIG. 7A is an enlarged cross-sectional view illustrating a first modification of the endoscope 100 illustrated in FIGS. 1 and 2. FIG. 7B is an enlarged perspective view illustrating the first modification of the endoscope 100 illustrated in FIGS. 1 and 2. The endoscope 100 of the first modification is an example of a case where electric power is transmitted to the imaging unit 120 by an electric field coupling method.

<Second Modification of Endoscope>

Figure 8A:
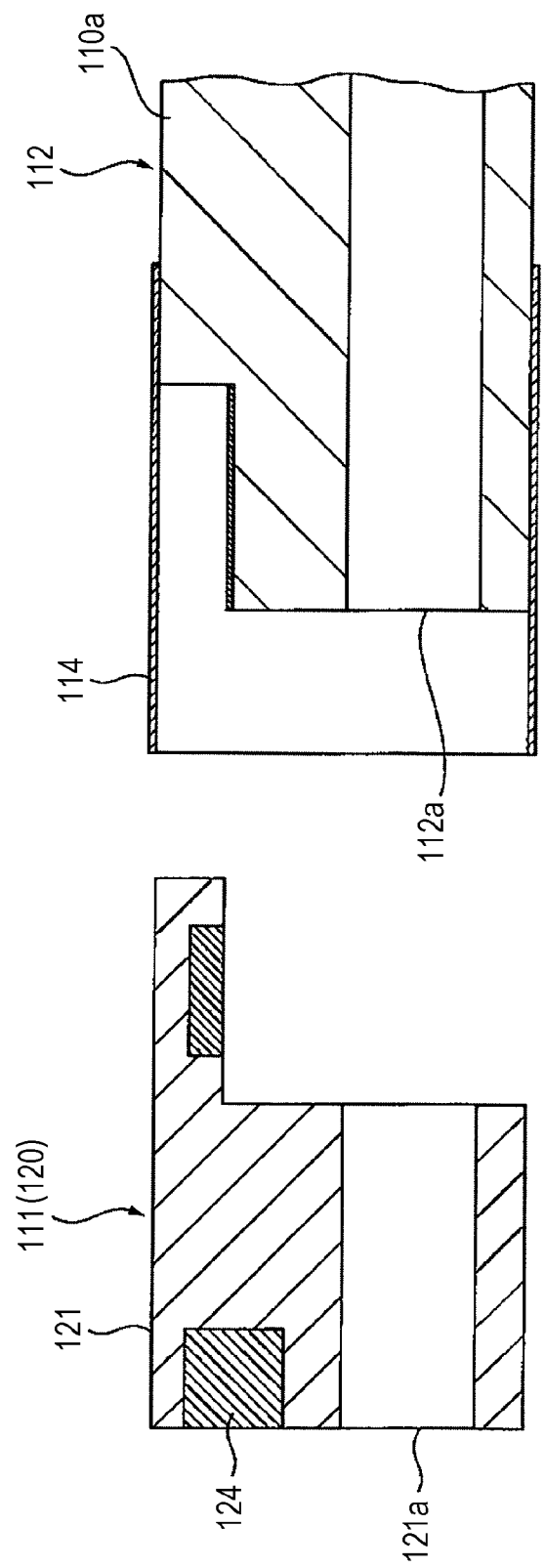
FIG. 8A is an enlarged cross-sectional view illustrating a second modification of the endoscope illustrated in FIGS. 1 and 2.
Figure 8B:
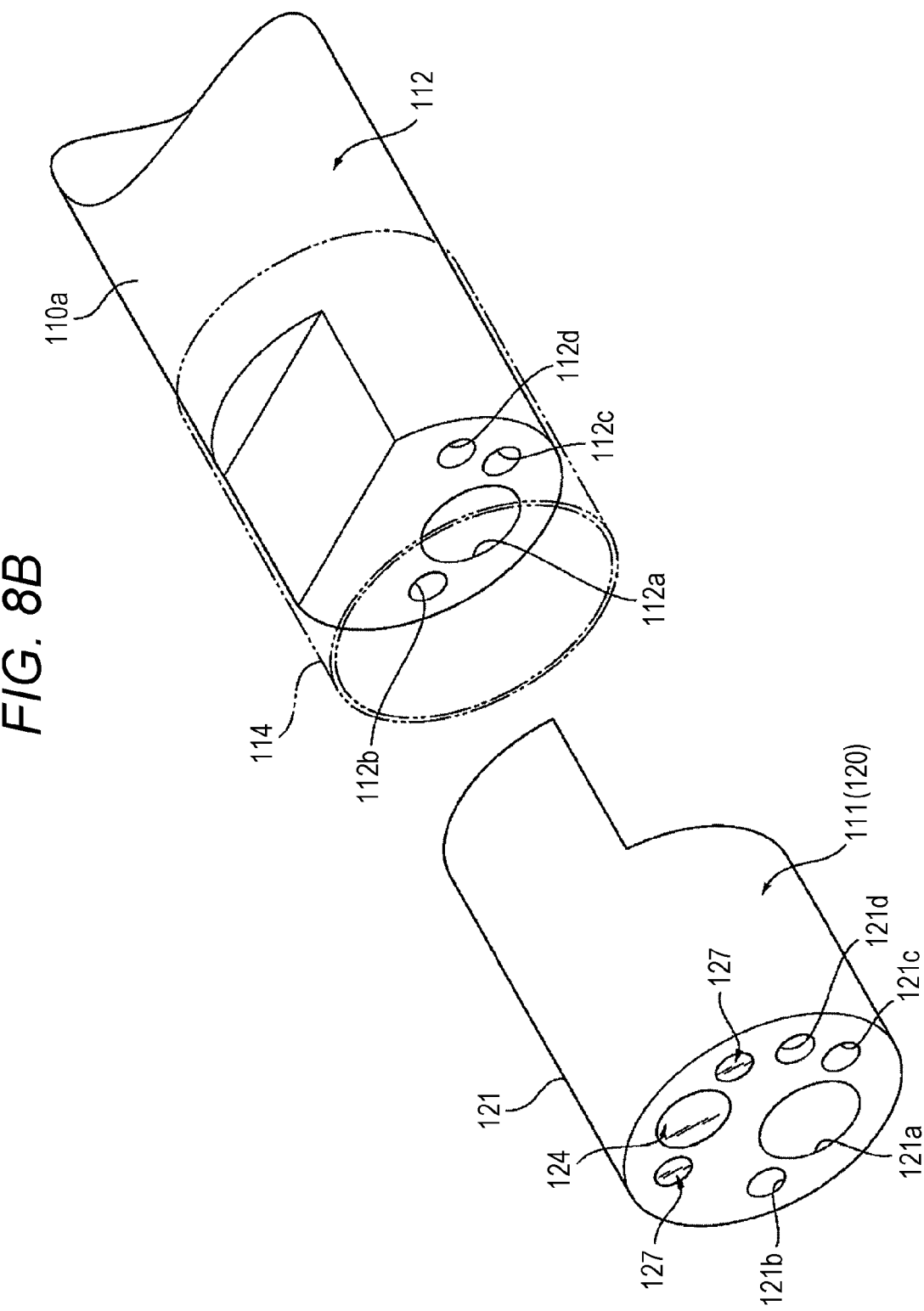
FIG. 8B is an enlarged perspective view illustrating the second modification of the endoscope illustrated in FIGS. 1 and 2.
Figure 9A:
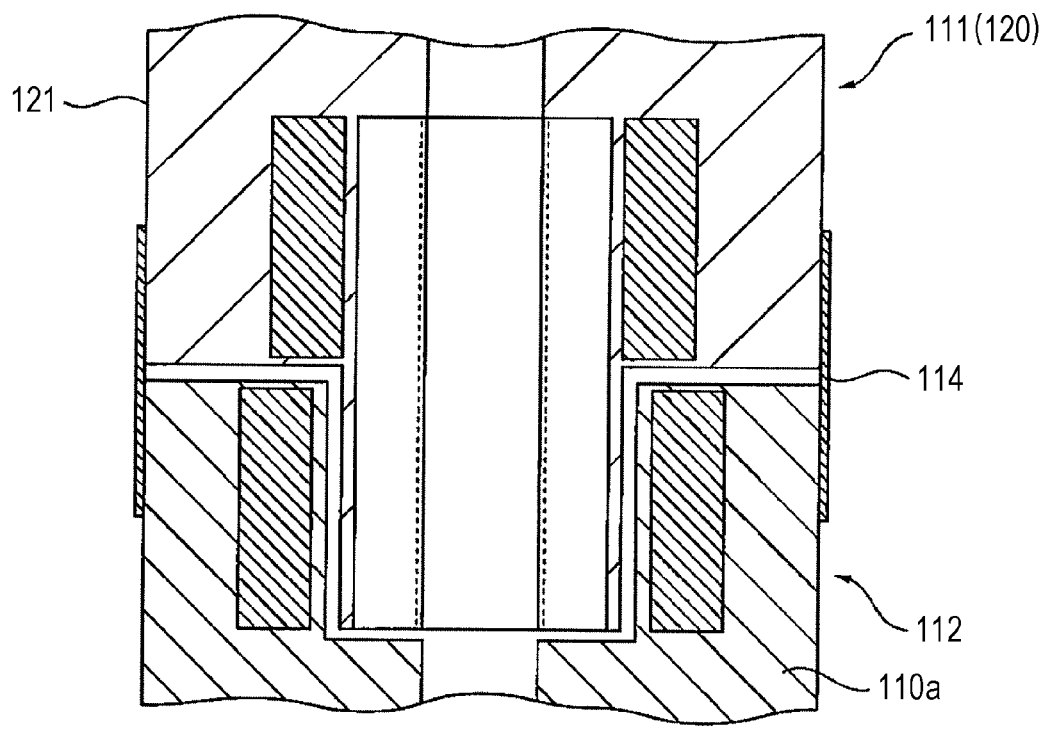
FIG. 9A is an enlarged cross-sectional view illustrating a third modification of the endoscope illustrated in FIGS. 1 and 2.
Figure 9B:
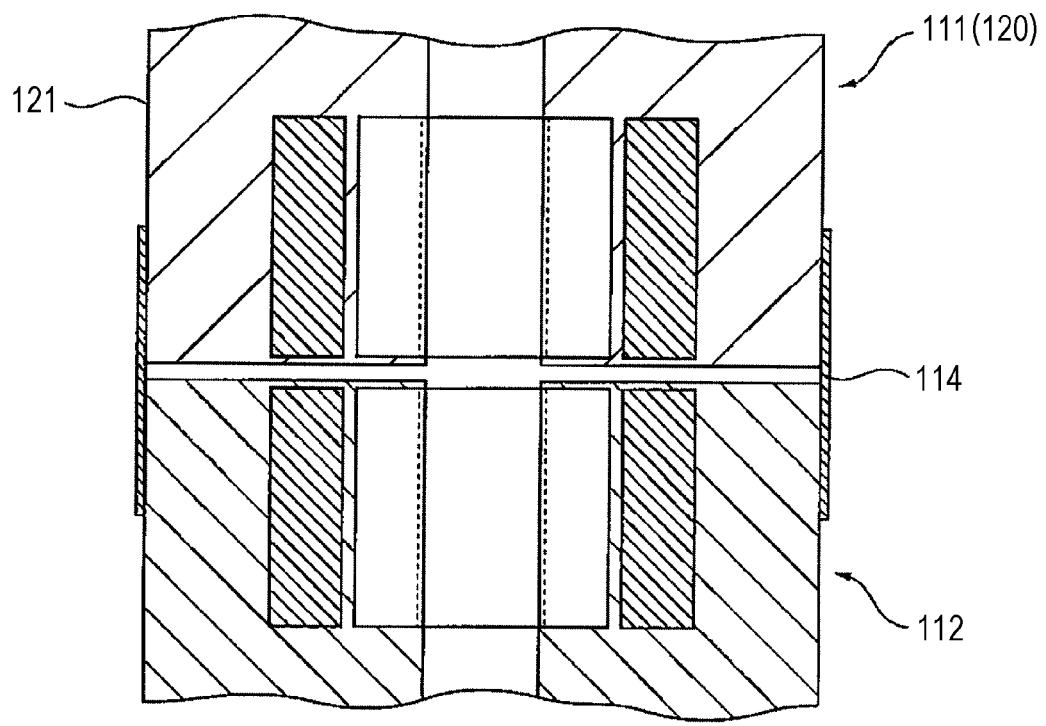
FIG. 9B is an enlarged cross-sectional view illustrating the third modification of the endoscope illustrated in FIGS. 1 and 2.
Figure 9C:
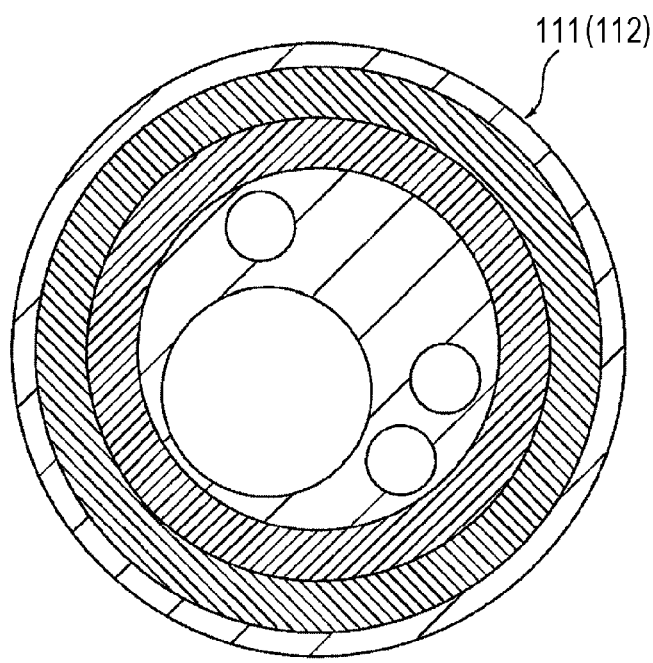
FIG. 9C is an enlarged cross-sectional view illustrating the third modification of the endoscope illustrated in FIGS. 1 and 2.
Figure 9D:
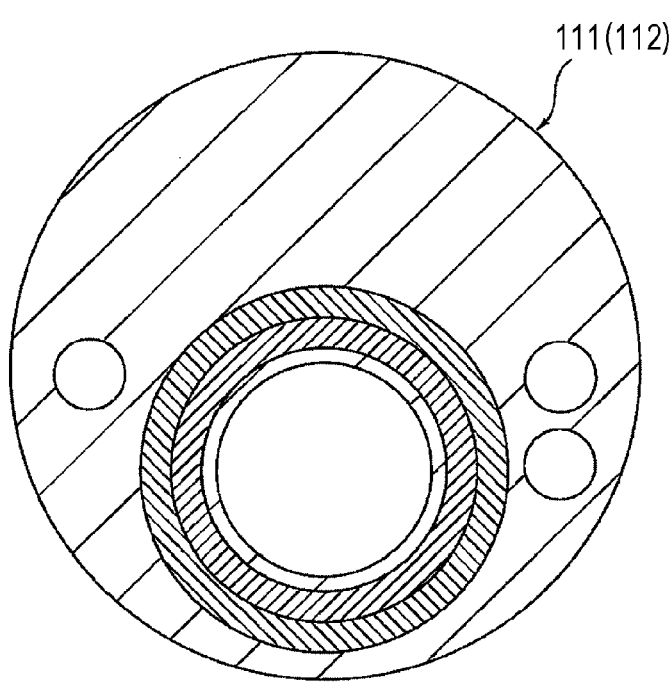
FIG. 9D is an enlarged cross-sectional view illustrating the third modification of the endoscope illustrated in FIGS. 1 and 2.

FIG. 8A is an enlarged cross-sectional view illustrating a second modification of the endoscope 100 illustrated in FIGS. 1 and 2. FIG. 8B is an enlarged perspective view illustrating the second modification of the endoscope 100 illustrated in FIGS. 1 and 2. The endoscope 100 of the second modification is an example of a case where electric power is transmitted to the imaging unit 120 by a two-dimensional communication method (evanescent wave method).

<Third Modification of Endoscope>

FIGS. 9A to 9D are cross-sectional views illustrating a third modification of the endoscope 100 illustrated in FIGS. 1 and 2. The endoscope 100 of the third modification is an example of a case where electric power is transmitted to the imaging unit 120 by an electromagnetic induction method. According to the endoscope 100 of this modification, it is possible to transmit electric power from the power transmission coil of the bending section 112 to the power reception coil of the imaging unit 120 by the electromagnetic induction method.

<Fourth Modification of Endoscope>

FIGS. 10A and 10B are enlarged cross-sectional views illustrating a fourth modification of the endoscope 100 illustrated in FIGS. 1 and 2. The endoscope 100 of the fourth modification is an example of a case where electric power or a signal is transmitted by an optical transmission method.

<Fifth Modification of Endoscope>

FIG. 11 is an enlarged cross-sectional view illustrating a fifth modification of the endoscope 100 illustrated in FIGS. 1 and 2. The endoscope 100 of the fifth modification may transmit electric power or a signal by a wireless transmission method.

Second Embodiment

This embodiment relates to the endoscope 100 in which the flexural rigidity changes at a rigidity changing position P1 provided at one position on the way of the soft portion 113. Descriptions regarding common parts with the first embodiment will be omitted.

Figure 12:
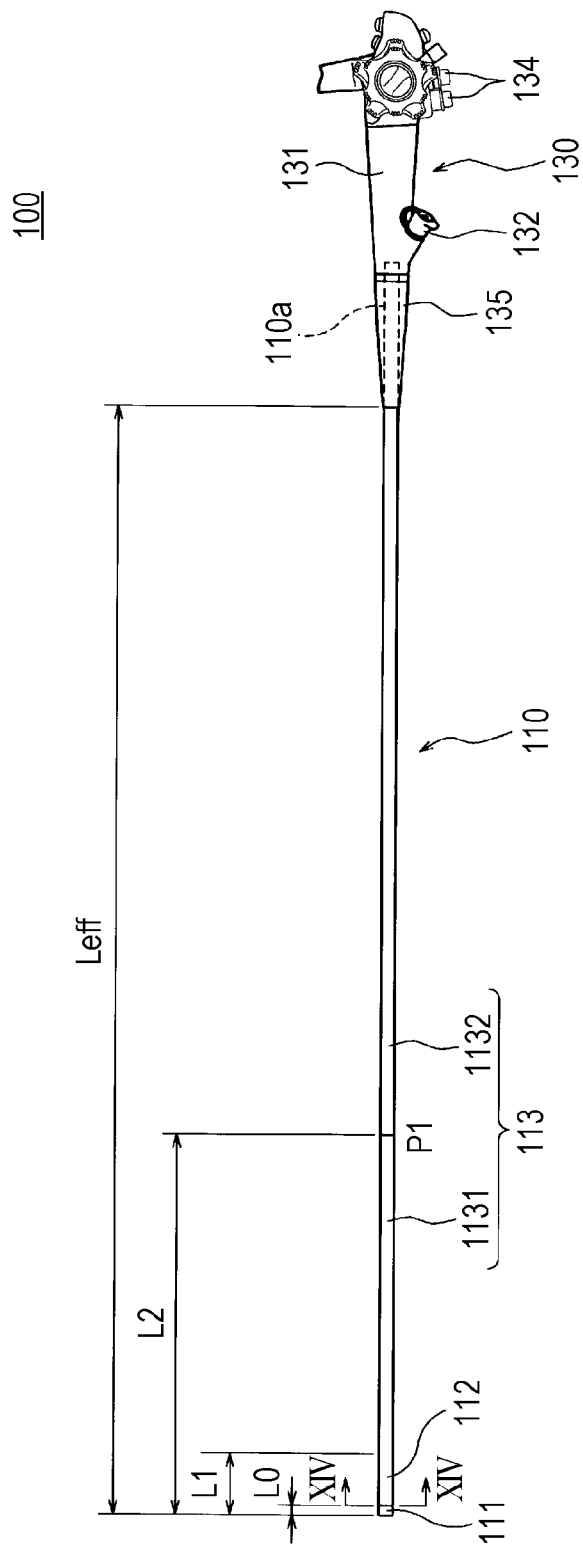
FIG. 12 is an explanatory diagram for explaining a configuration of an insertion portion of an endoscope according to a second embodiment.

FIG. 12 is an explanatory diagram for explaining a configuration of the insertion portion 110 of the endoscope 100 according to the second embodiment. In FIG. 12, the connector cable 140 and the connector unit 150 are not illustrated.

As described above, the insertion portion 110 includes the resin tube 110a. The tube 110a is a multi-lumen tube provided with a plurality of through holes penetrating in the longitudinal direction. One end of the tube 110a is covered with the distal tip 111. The other end of the tube 110a is attached to the inside of the operation unit body 131 through a folding portion 135.

In the following description, the distance from the distal tip of the insertion portion 110 to the boundary between the distal tip 111 and the bending section 112 is referred to as a distance L0. Similarly, the distance from the distal tip of the insertion portion 110 to the boundary between the bending section 112 and the soft portion 113 is referred to as a distance L1. The distance from the distal tip of the insertion portion 110 to the rigidity changing position P1 where the flexural rigidity of the insertion portion 110 changes is referred to as L2. The distance from the distal tip of the insertion portion 110 to the distal tip of the folding portion 135, that is, the effective length of the endoscope 100 is referred to as Leff.

Figure 13:
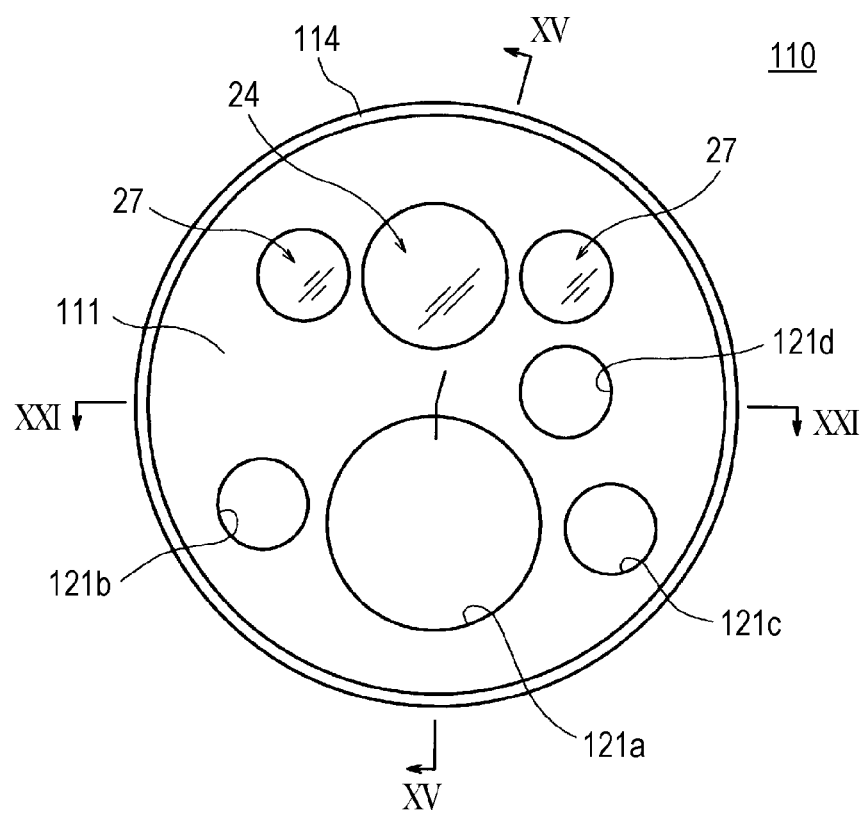
FIG. 13 is an exterior view of a distal tip of the insertion portion of the second embodiment.

FIG. 13 is an exterior view of the distal tip of the insertion portion 110 according to the second embodiment. The distal tip 111 has a cylindrical shape having an outer diameter substantially the same as that of the tube 110a. The distal tip 111 covers the end surface of the tube 110a.

The forceps port 121a, the air supply port 121b, the water supply port 121c, the auxiliary water supply port 121d, an observation window 24, and two illumination windows 27 are arranged at the distal tip 111. The observation window 24 is arranged between the two illumination windows 27. The imaging unit 120 including the image sensor 124 is arranged on the back side of the observation window 24. The small LED illumination 127 is arranged on the back side of the illumination window 27.

The forceps port 121a, the air supply port 121b, the water supply port 121c, and the auxiliary water supply port 121d are through holes provided at the distal tip 111. The air supply port 121b, the water supply port 121c, and the auxiliary water supply port 121d are arranged around the forceps port 121a. The air supply port 121b and the water supply port 121c may be provided with nozzles that direct the jetted water and air toward the observation window 24 side.

Figure 14:
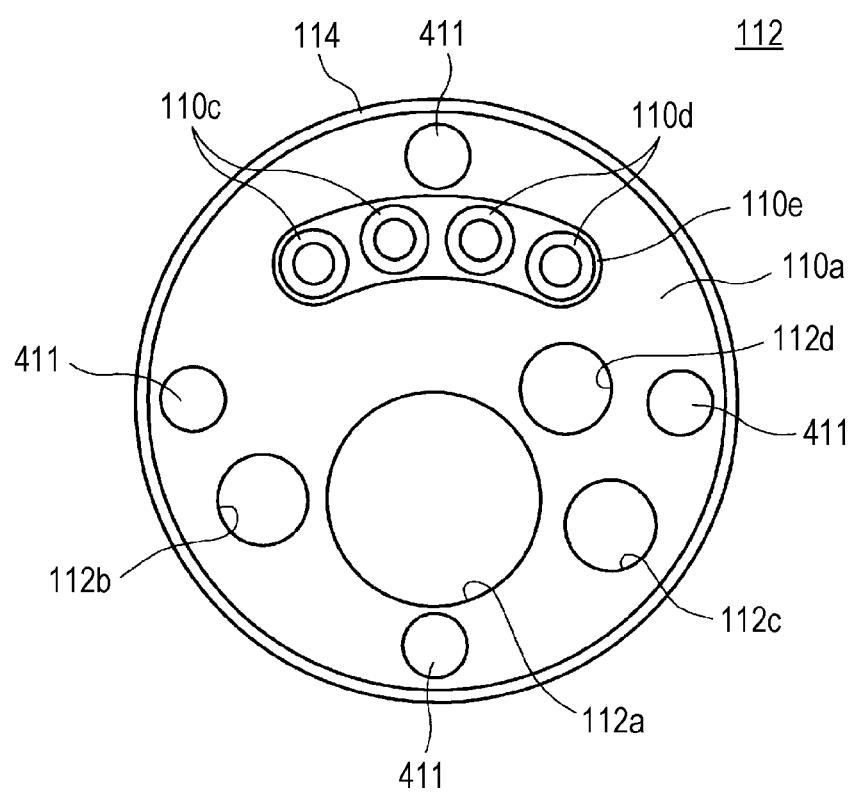
FIG. 14 is a cross-sectional view taken along line XIV-XIV in FIG. 12.

FIG. 14 is a cross-sectional view taken along line XIV-XIV in FIG. 12. FIG. 14 illustrates the front end surface of the bending section 112. At a position close to the outer circumference of the tube 110a that forms the bending section 112, retaining portions 411 provided at the distal tips of the four angle wires 41 are embedded at substantially equal intervals.

A holding block 110e that holds two power source connectors 110c and two signal connectors 110d is embedded closer to the central axis side of the tube 110a than the upper retaining portion 411 in FIG. 14. The power source connector 110c is arranged at a position corresponding to the power source pin 122 described using FIG. 5. The signal connector 110d is arranged at a position corresponding to the signal pin 123 described using FIG. 5.

Four openings from the opening 112a to the opening 112d are arranged on the end surface of the bending section 112. The opening 112a is provided at a position corresponding to the forceps port 121a, and has an inner diameter substantially equal to that of the forceps port 121a. The opening 112b is provided at a position corresponding to the air supply port 121b, and has an inner diameter substantially equal to that of the air supply port 121b.

The opening 112c is provided at a position corresponding to the water supply port 121c, and has an inner diameter substantially equal to that of the water supply port 121c. The opening 112d is provided at a position corresponding to the auxiliary water supply port 121d, and has an inner diameter substantially equal to that of the auxiliary water supply port 121d.

Figure 15:
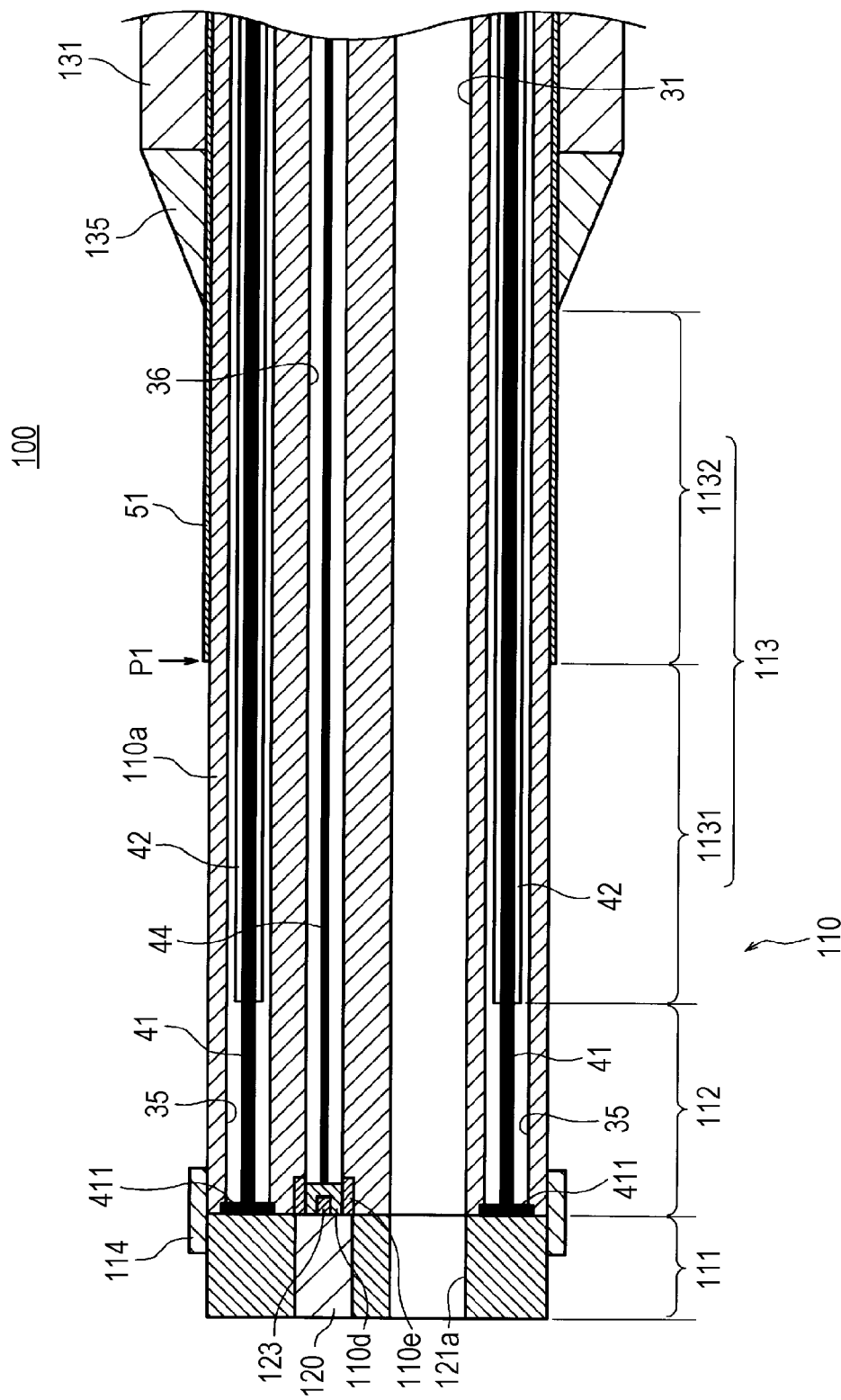
FIG. 15 is a schematic view of a cross section taken along line XV-XV in FIG. 13.

FIG. 15 is a schematic view of a cross section taken along line XV-XV in FIG. 13. In FIG. 15, the longitudinal direction of the insertion portion 110 is reduced to schematically illustrate the structure. Further, the illustration of the observation window 24 covering the cross section of the imaging unit 120 and the surface of the imaging unit 120 is omitted.

The distal tip 111 is arranged on the end surface of the tube 110a. The signal pin 123 protruding from the distal tip 111 is inserted into the signal connector 110d held by the holding block 110e. Similarly, the power source pin 122 is inserted into the power source connector 110c. The power source pin 122 and the power source connector 110c, and the signal pin 123 and the signal connector 110d are held by contacts (not illustrated) so as to be electrically connected and at the same time not to be easily removed.

The joint between the tube 110a and the distal tip 111 is covered by the fractured portion 114. The fractured portion 114 is formed of, for example, a heat-shrinkable tube, a tape with an adhesive material, or an adhesive agent which is applied in a predetermined range and then cured. The end surface of the tube 110a and the distal tip 111 may be adhesively fixed. In this case, the adhesive layer interposed between the tube 110a and the distal tip 111 also forms the fractured portion 114.

When the tube 110a and the distal tip 111 can be bonded with sufficient strength, the fractured portion 114 that covers the joint between the tube 110a and the distal tip 111 may not be provided. In this case, only the adhesive layer interposed between the tube 110a and the distal tip 111 forms the fractured portion 114.

By breaking the fractured portion 114, the distal tip 111 can be separated from the endoscope 100 without being damaged. The separated distal tip 111 can be reused when assembling a new endoscope 100. That is, the distal tip 111 performs the function of the reusable portion R in which it is reused, and the function of the single-use portion S in which the other portion is disposed after being used once.

In addition, when the end surface of the tube 110a and the distal tip 111 are bonded and fixed, it is desirable to use an adhesive that can be easily peeled off at a predetermined temperature or by using a predetermined solvent or the like. The predetermined temperature or the predetermined solvent is a temperature or a solvent that is not used in a medical institution during an endoscopic examination. By doing so, it is possible to provide the endoscope 100 in which the distal tip 111 can be removed without damage.

Figure 16:
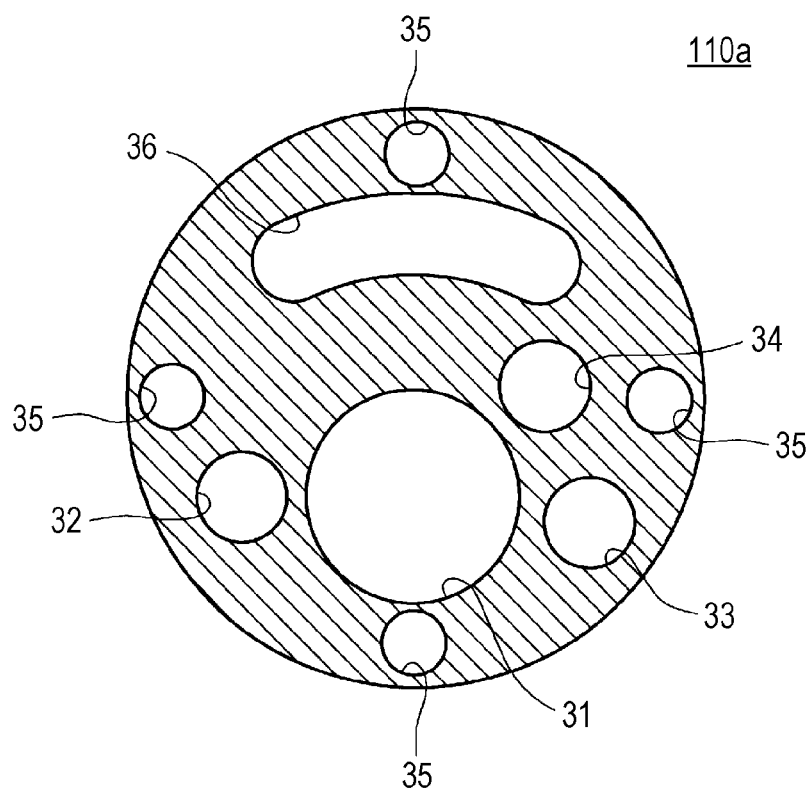
FIG. 16 is a cross-sectional view of a tube.

FIG. 16 is a cross-sectional view of the tube 110a. The tube 110a is a multi-lumen tube manufactured by resin extrusion molding, and has the same cross-sectional shape over the entire length. The tube 110a includes the treatment tool channel 31, the air supply channel 32, the water supply channel 33, the auxiliary water supply channel 34, the four wire channels 35, and the cable channel 36. Each channel is an example of the channel 110b described in the first embodiment.

The treatment tool channel 31, the air supply channel 32, the water supply channel 33, the auxiliary water supply channel 34, and the wire channel 35 have a circular cross section. The end portion of the treatment tool channel 31 forms the forceps port 121a. The end portion of the air supply channel 32 forms the air supply port 121b. The end portion of the water supply channel 33 forms the water supply port 121c. The end portion of the auxiliary water supply channel 34 forms the auxiliary water supply port 121d.

The description will be continued using FIGS. 15 and 16. The wire sheath 42 is inserted through the wire channel 35. The angle wire 41 is inserted through the wire sheath 42. The distal tip of the angle wire 41 projects from the wire sheath 42. The portion of the angle wire 41 not covered by the wire sheath 42 forms the bending section 112, and the portion of the angle wire 41 covered by the wire sheath 42 forms the soft portion 113.

The wire sheath 42 is, for example, a tight coil or a flexible tube. The wire sheath 42 is an example of the rigid member described in the first embodiment. One end of the wire sheath 42 is fixed to the operation unit body 131. The wire sheath 42 may be fixed to the inner wall of the wire channel 35 over the entire length of the soft portion 113.

The thick diameter retaining portion 411 is provided at one end of the angle wire 41. The retaining portion 411 is fitted into the end portion of the wire channel 35. The other end of the angle wire 41 is connected to a bending mechanism (not illustrated) inside the operation unit body 131.

When the user operates the bending mechanism, the angle wire 41 moves back and forth in the wire sheath 42 in the longitudinal direction. By pulling the angle wire 41 toward the operation unit side, the portion where the angle wire 41 projects from the wire sheath 42 becomes shorter. As a result, the bending section 112 bends toward the pulled-in angle wire 41 side.

The inner surface of the forceps port 121a and the inner surface of the treatment tool channel 31 smoothly communicate with each other to form a channel that is a passage of the treatment tool. The treatment tool inserted by the user from the treatment tool inlet 132 projects from the distal tip of the insertion portion 110 via the treatment tool channel 31 and the forceps port 121a.

Although illustration is omitted, the inner surface of the air supply port 121b and the inner surface of the air supply channel 32 are in smooth communication. The inner surface of the water supply port 121c and the inner surface of the water supply channel 33 are in smooth communication. The inner surface of the auxiliary water supply port 121d and the inner surface of the auxiliary water supply channel 34 are in smooth communication.

The cable channel 36 has a substantially oval cross section. A cable 44 is inserted through the cable channel 36. The end portion of the cable 44 is connected to the power source connector 110c and the signal connector 110d. In the end portion of the cable channel 36, the power source connector 110c and the signal connector 110d are embedded in a holding block 110e.

A power source cable that supplies power to the image sensor 124 is connected to the power source connector 110c. A signal cable for transmitting a signal between the image sensor 124 and the processor 3 is connected to the signal connector 110d. In the following description, the power source cable and the signal cable may be collectively referred to as the cable 44.

A driver IC and a multiplexer may be arranged between the cable 44 and the power source connector 110c and the signal connector 110d. The numbers of cables 44, power source connectors 110c, and signal connectors 110d are arbitrary. One cable channel 36 having a circular cross section may be provided for one cable 44. The cable channel 36 for the power cable 44 and the cable channel 36 for the signal cable 44 may be provided separately.

The distal tip 111 does not have an opening at a location corresponding to the wire channel 35 and the cable channel 36. The distal tip 111 covers the end portions of the wire channel 35 and the cable channel 36.

The operation unit side of the insertion portion 110 is covered with an outer cover 51. The outer cover 51 is, for example, a heat shrinkable tube or an elastic resin tube. The outer cover 51 may be a layer formed by spirally winding an adhesive tape around the tube 110a. The outer cover 51 may be a layer obtained by spirally winding a resin tape around the tube 110a and then heating and fusing the resin tape. The outer cover 51 may be a layer in which a liquid resin material is applied to the outer peripheral surface of the tube 110a and cured.

The flexural rigidity of the portion of the soft portion 113 covered with the outer cover 51 may be higher than the flexural rigidity of the portion which is not covered with the outer cover 51. Therefore, the boundary between the portion covered with the outer cover 51 and the portion not covered with the outer cover 51 forms the rigidity changing position P1 described using FIG. 12. A portion of the soft portion 113 which is not covered with the outer cover 51 forms a first region 1131 and a portion which is covered with the outer cover 51 forms a second region 1132.

The configuration of the endoscope 100 described with reference to FIGS. 12 to 16 is an example. The endoscope 100 may not have a part or all of the forceps port 121a, the air supply port 121b, the water supply port 121c, and the auxiliary water supply port 121d. The endoscope 100 may have a plurality of forceps ports 121a. The number of the angle wires 41 may be two or one. The number of small LED illuminations 127 may be one or three or more.

Figure 17:
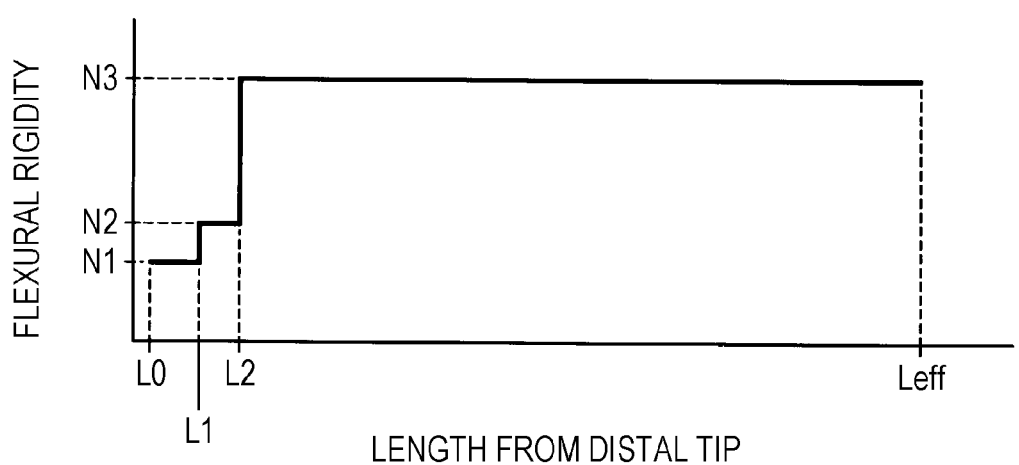
FIG. 17 is a graph for explaining flexural rigidity of a bending section and a soft portion according to the second embodiment.

FIG. 17 is a graph illustrating flexural rigidity of the bending section 112 and the soft portion 113 according to the second embodiment. The horizontal axis represents the length from the distal tip of the insertion portion 110. The vertical axis represents the flexural rigidity of the bending section 112 and the soft portion 113. The flexural rigidity is not defined because the distal tip 111 is rigid.

L0, L1, L2, and Leff indicate the lengths from the distal tip of the insertion portion 110 described using FIG. 12, respectively. N1 indicates the flexural rigidity of the bending section 112. N2 indicates the flexural rigidity of the first region 1131. N3 indicates the flexural rigidity of the second region 1132. N1, N2, and N3 satisfy the relationship of Expression (1).

$$N1<N2<N3 \tag{1}$$

A method of measuring the flexural rigidity of the bending section 112 and the soft portion 113 will be described. The measuring instrument used for the measurement is the same as the measuring instrument described using FIG. 4. The rollers W1 and W2 are arranged in line symmetry with an indentation direction of the measuring rod L of the measuring instrument M as the axis of symmetry. The central axis of the roller W3 is arranged on this axis of symmetry.

The amount D1 of indentation and the distance D2 between the rollers W1 in FIG. 4 are set to the values illustrated in Table 3.

TABLE 3

| Outer diameter of insertion portion | D1 | D2 |
|---|---|---|
| 7.0 mm or less | 25 mm | 100 mm |
| Exceeding 7.0 mm | 20 mm | 200 mm |

The roller W2 is arranged so as to prevent the object to be measured outside the roller W1 from moving in the direction opposite to the indentation direction when the measuring rod L is pushed in. As long as this function is fulfilled, the distance between the rollers W2 is arbitrary. The above function can be realized by setting the distance between the rollers W2 to a value around from D2+2d to d2+4d when the outer diameter of the object to be measured is indicated by d.

Incidentally, when a portion having an outer diameter of 7.0 mm or less and a portion exceeding 7.0 mm coexist in the insertion portion 110 of one endoscope 100, both portions are measured using the condition when the outer diameter of any portion is 7.0 mm or less.

A case where the flexural rigidity N1 of the bending section 112 is measured will be described. The tube 110a that is sufficiently longer than the distance between the rollers W2 is prepared. The angle wire 41 and the cable 44, which are longer than the tube 110a, are inserted into the tube 110a. Through the above steps, the measurement sample is completed.

The measurement sample is arranged between the roller W1 and the roller W2 in the state of being straightened as described using FIG. 4. The reaction force when the roller W3 is pushed in by a predetermined amount D1 of indentation is the flexural rigidity of the bending section 112.

A case of measuring the flexural rigidity N2 of the first region 1131 will be described. The first region 1131 is straightened. When the first region 1131 is sufficiently long, the first region 1131 is arranged between the rollers W2. When the first region 1131 is shorter than the interval between the rollers W2 and longer than the interval between the rollers W1, the central portion of the first region 1131 is arranged so as to be located at the central portion between the rollers W1. The reaction force when the roller W3 is pushed in by a predetermined amount D1 of indentation is the flexural rigidity of the first region 1131.

When the first region 1131 is shorter than the distance between the rollers W1, the tube 110a that is sufficiently longer than the distance between the rollers W2 is prepared. The wire sheath 42, the angle wire 41, and the cable 44, which are longer than the tube 110a, are inserted into the tube 110a. Through the above steps, the measurement sample is completed.

The measurement sample is arranged between the roller W1 and the roller W2 in the state of being straightened as described using FIG. 4. The reaction force when the roller W3 is pushed in by a predetermined amount D1 of indentation is the flexural rigidity of the first region 1131.

A case where the flexural rigidity N3 of the second region 1132 is measured will be described. Generally, the second region 1132 is longer than the distance between the rollers W2. The second region 1132 extends straightly. The second region 1132 is arranged between the rollers W2. The reaction force when the roller W3 is pushed in by a predetermined amount D1 of indentation is the flexural rigidity of the second region 1132.

When the endoscope 100 can be disassembled for measurement, measurement is performed according to the following procedure. First, the flexural rigidity of the second region 1132 is measured. When the first region 1131 is longer than the interval between the rollers W1, the flexural rigidity of the first region 1131 is measured by the procedure described above.

When the first region 1131 is shorter than the interval between the rollers W1, the outer cover 51 is removed from the side closer to the first region 1131 and the portion having the same configuration as the first region 1131 is increased. After securing a sufficient length for the portion having the same structure as the first region 1131, the flexural rigidity of the first region 1131 is measured.

After that, the insertion portion 110 is removed from the operation unit 130, or the insertion portion 110 is cut at a position close to the operation unit 130. The wire sheath 42 is removed to secure a sufficient length for the portion having the same configuration as the bending section 112.

After that, the flexural rigidity of the bending section 112 is measured in the same procedure as the above-mentioned first region 1131.

Tables 4 and 5 illustrate examples of suitable endoscopes 100. The unit of the tube outer diameter, L1, L2 and Leff is mm. The unit of N1, N2 and N3 is Newton. L0 is about 10 mm to 20 mm.

TABLE 4

| No. | 1 | 2 | 3 |
|---|---|---|---|
| Outer diameter of tube | 5.5 | 9 | 11.5 |
| L1 | 700 | 74 | 86 |
| L2 | 200 | 200 | 200 |
| Leff | 1050 | 1050 | 1050 |
| N1 | 1.25 | 2 | 2.5 |
| N2 | 2.8 | 4.5 | 6 |
| N3 | 3.5 | 5.5 | 8 |

Table 4 indicates the endoscope 100 for the upper digestive tract. No. 1 indicates the endoscope 100 for the upper digestive tract, which is suitable for nasal insertion and pediatric use. No 2 indicates the endoscope 100 suitable for general upper endoscopic examination. No 3 indicates the endoscope 100 suitable for endoscopic treatment and the like.

TABLE 5

| No. | 4 | 5 | 6 |
|---|---|---|---|
| Outer diameter of tube | 5.1 | 5.1 | 3.3 |
| L1 | 50 | 50 | 25 |
| L2 | 80 | 80 | 51 |
| Leff | 600 | 400 | 1900 |
| N1 | 1.5 | 1.5 | 1.25 |
| N2 | 2.25 | 2.25 | 1.75 |
| N3 | 5 | 5 | 2.5 |

Table 5 indicates a respiratory endoscope 100 and a urinary endoscope 100. No. 4 indicates the endoscope 100 for a respiratory organ. Compared to the endoscope 100 for the upper digestive tract illustrated in No. 1 to No. 3, the effective length Leff is short and the flexural rigidity is small. Since the flexural rigidity is small, it is possible to provide the endoscope 100 that smoothly bends along the bronchus even when it is inserted into the bronchus that extends toward the upper lobe of the lung.

No. 5 indicates the endoscope 100 for urology. The effective length Leff is even shorter than that of the respiratory endoscope 100 indicated in No. 4. No. 6 indicates the endoscope 100 for a so-called baby scope. Since it is inserted into the pancreaticobiliary duct via the channel of the endoscope 100 for duodenum, it has a small outer diameter and a long effective length Leff.

Note that No. 1 to No. 6 are all examples, and the specifications and uses of the endoscope 100 are not limited to these.

<First Example of Second Modification of Endoscope>

A first example of the second modification of the second embodiment relates to the endoscope 100 in which the outer cover 51 has the function of the fractured portion 114. Descriptions regarding common parts with the second embodiment will be omitted.

Figure 18:
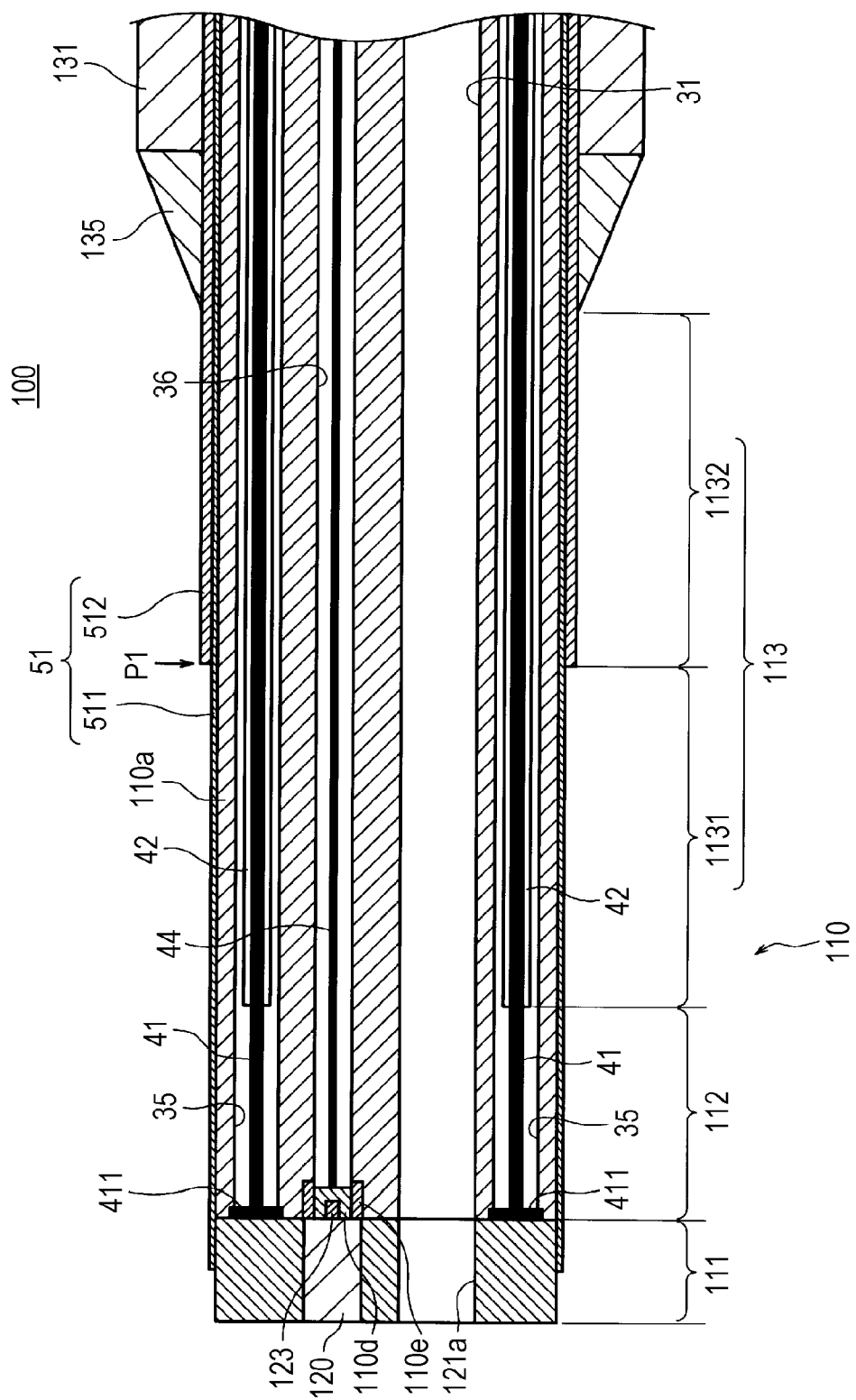
FIG. 18 is a schematic view for explaining a first example of the second modification of the insertion portion of the second embodiment.

FIG. 18 is a schematic view for explaining the first example of the second modification of the insertion portion 110 according to the second embodiment. FIG. 18 illustrates a cross section similar to that of FIG. 15.

The outer cover 51 of this modification example includes a first outer cover 511 and a second outer cover 512. The first outer cover 511 continuously covers about half of the outer peripheral surface of the distal tip 111 on the operation unit side and the outer peripheral surface of the tube 110a. The second outer cover 512 covers the first outer cover 511 on the operation unit side of the insertion portion 110.

The first outer cover 511 and the second outer cover 512 are made of the same material and manufacturing method as outer cover 51 of the second embodiment. The material and manufacturing method of the first outer cover 511 and the second outer cover 512 may be the same or different.

The portion of the first outer cover 511 that covers the joint between the tube 110a and the distal tip 111 serves as the fractured portion 114 of this modification. The flexural rigidity of the portion of the soft portion 113 covered with the two layers of the first outer cover 511 and the second outer cover 512 is higher than the flexural rigidity of the portion covered with only the first outer cover 511. Therefore, the boundary between the portion covered with the second outer cover 512 and the portion not covered with the second outer cover 512 forms the rigidity changing position P1 described using FIG. 12.

Similarly, the portion of the soft portion 113 that is covered only with the first outer cover 511 forms the first region 1131, and the portion that is covered with two layers of the first outer cover 511 and the second outer cover 512 forms the second region 1132.

According to this modification, the first outer cover 511 can provide the endoscope 100 in which the flexural rigidity of the bending section 112 and the first region 1131 is enhanced.

<Second Example of Second Modification of Endoscope>

A second example of the second modification of the second embodiment relates to the endoscope 100 in which the outer cover 51 has the function of the fractured portion 114. Descriptions regarding common parts with the second embodiment will be omitted.

Figure 19:
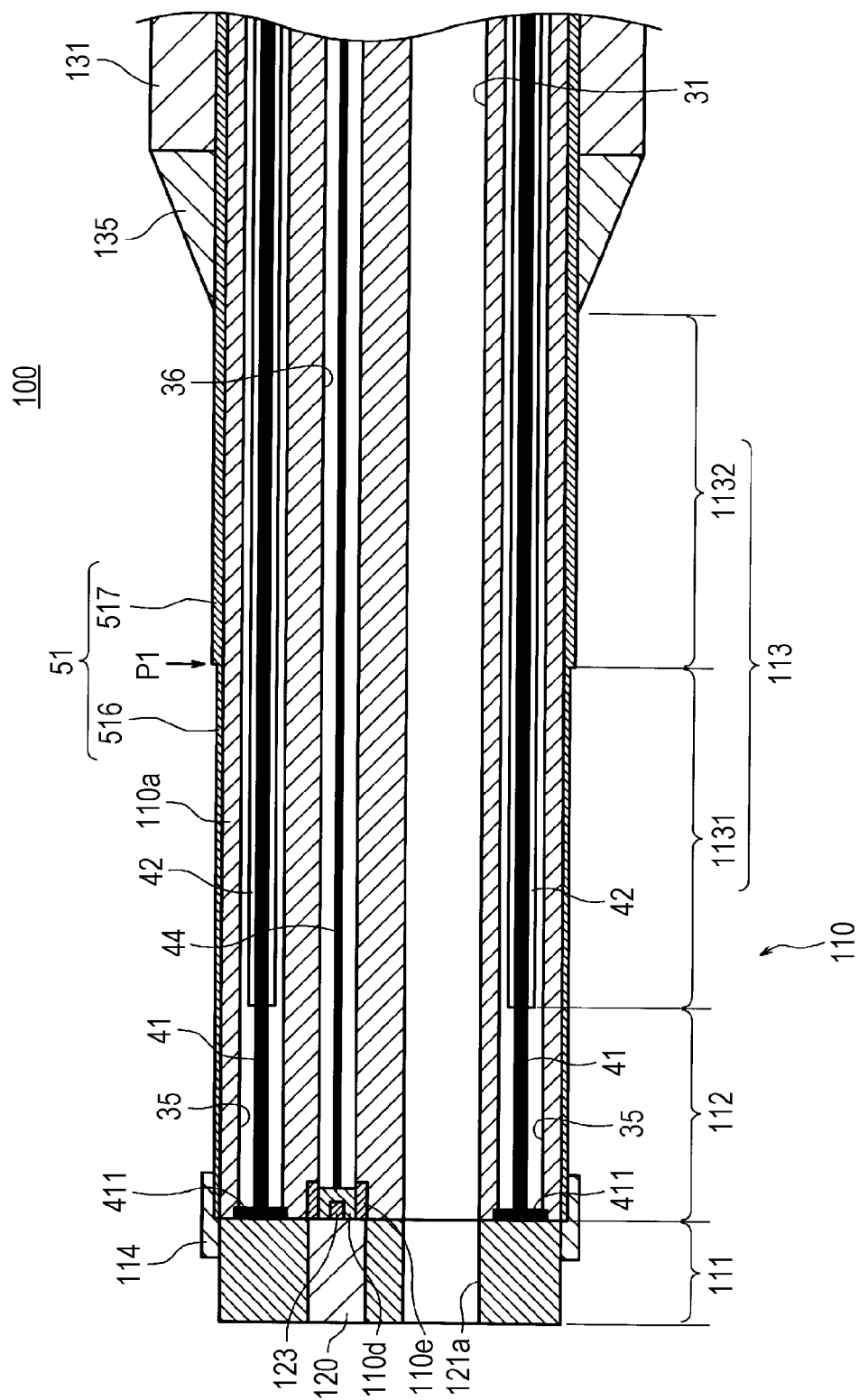
FIG. 19 is a schematic view for explaining a second example of the second modification of the insertion portion of the second embodiment.

FIG. 19 is a schematic view for explaining the second example of the second modification of the insertion portion of the second embodiment. FIG. 19 illustrates a cross section similar to that of FIG. 15.

The outer cover 51 of this modification includes a thin region 516 and a thick region 517. The thin region 516 covers the distal tip side portion of the outer peripheral surface of the tube 110a. The thick region 517, which is thicker than the thin region 516, covers a portion of the outer peripheral surface of the tube 110a that is not covered by the thin region 516. The thin region 516 and the thick region 517 are integrally formed.

The flexural rigidity of the portion of the soft portion 113 that is covered by the thick region 517 is higher than the flexural rigidity of the portion covered by the thin region 516. Therefore, the boundary between the thin region 516 and the thick region 517 forms the rigidity changing position P1 described using FIG. 12. Similarly, the portion of the soft portion 113 covered by the thin region 516 forms the first region 1131, and the portion covered by the thick region 517 forms the second region 1132.

According to this modification, the material of the surface of the insertion portion 110 does not change before and after the rigidity changing position P1. It is possible to provide the endoscope 100 in which when a doctor who is a user inserts the insertion portion 110 into a patient, it is difficult for the doctor to feel discomfort such as a change in surface slipperiness.

<Third Example of Second Modification of Endoscope>

A third example of the second modification of the second embodiment relates to the endoscope 100 in which the outer cover 51 has the function of the fractured portion 114. Descriptions regarding common parts with the second embodiment will be omitted.

Figure 20:
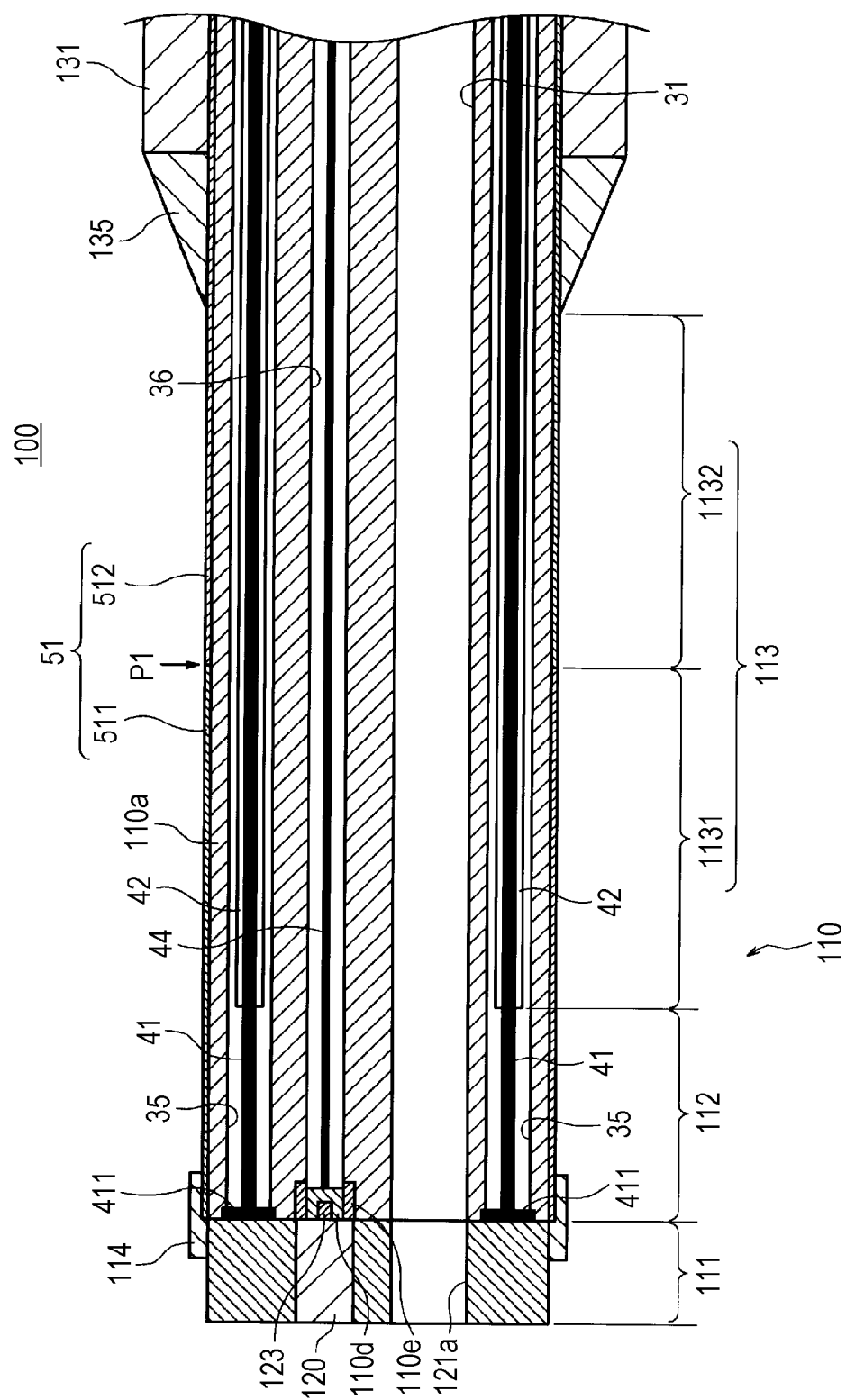
FIG. 20 is a schematic view illustrating a third example of the second modification of the insertion portion of the second embodiment.

FIG. 20 is a schematic view for explaining the third example of the second modification of the insertion portion 110 of the second embodiment. FIG. 20 illustrates a cross section similar to that of FIG. 15.

The outer cover 51 of this modification example includes a first outer cover 511 and a second outer cover 512. The first outer cover 511 covers the distal tip side portion of the outer peripheral surface of the tube 110a. The second outer cover 512 covers the portion of the outer peripheral surface of the tube 110a that is not covered with the first outer cover 511. The second outer cover 512 is formed of a material harder than the first outer cover 511. The first outer cover 511 and the second outer cover 512 have almost the same thickness.

The flexural rigidity of the portion of the soft portion 113 covered with the second outer cover 512 is higher than the flexural rigidity of the portion covered with the first outer cover 511. Therefore, the boundary between the portion covered with the first outer cover 511 and the portion covered with the second outer cover 512 forms the rigidity changing position P1 described using FIG. 12. The portion of the soft portion 113 covered with the first outer cover 511 forms the first region 1131, and the portion covered with the second outer cover 512 forms the second region 1132.

According to this modification, the thickness of the insertion portion 110 hardly changes before and after the rigidity changing position P1. It is possible to provide the endoscope 100 in which when a doctor who is a user inserts the insertion portion 110 into a patient, it is difficult for the doctor to feel discomfort due to a change in the thickness of the insertion portion 110.

<Fourth Example of Second Modification of Endoscope>

A fourth example of the second modification of the second embodiment relates to the endoscope 100 in which the distal tip 111 includes the fixing protrusion 54. Descriptions regarding common parts with the second embodiment will be omitted.

Figure 21:
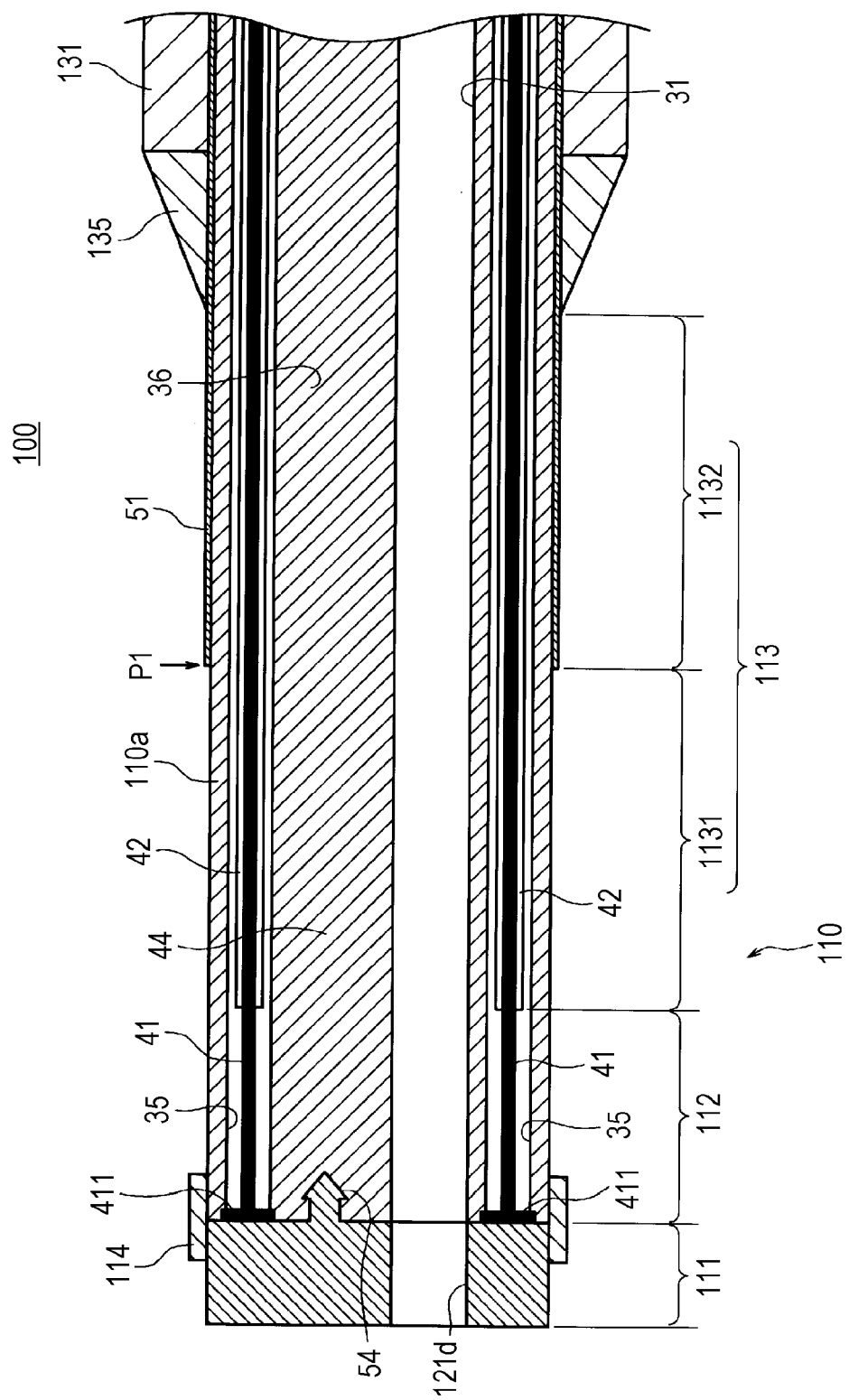
FIG. 21 is a schematic view illustrating a fourth example of the second modification of the insertion portion of the second embodiment.

FIG. 21 is a schematic view for explaining the fourth example of the second modification of the insertion portion of the second embodiment. FIG. 21 illustrates a cross section corresponding to the cross section taken along line XX1-XXI in FIG. 13.

The distal tip 111 includes a fixing protrusion 54 that protrudes from the surface on the tube 110a side. The fixing protrusion 54 has a sharp distal tip and has a retainer. The fixing protrusion 54 pierces the end surface of the tube 110a and fixes the distal tip 111 to the tube 110a.

Note that FIG. 21 exemplifies a case where the number of the fixing protrusions 54 is one, but the distal tip 111 may include a plurality of fixing protrusions 54. According to this embodiment, it is possible to provide the endoscope 100 in which the distal tip 111 and the tube 110a are firmly joined.

Third Embodiment

This embodiment relates to the endoscope 100 in which the flexural rigidity changes at two positions, a rigidity changing position P1 and a rigidity changing position P2, which are provided in the middle of the soft portion 113. Descriptions regarding common parts with the second embodiment will be omitted.

Figure 22:
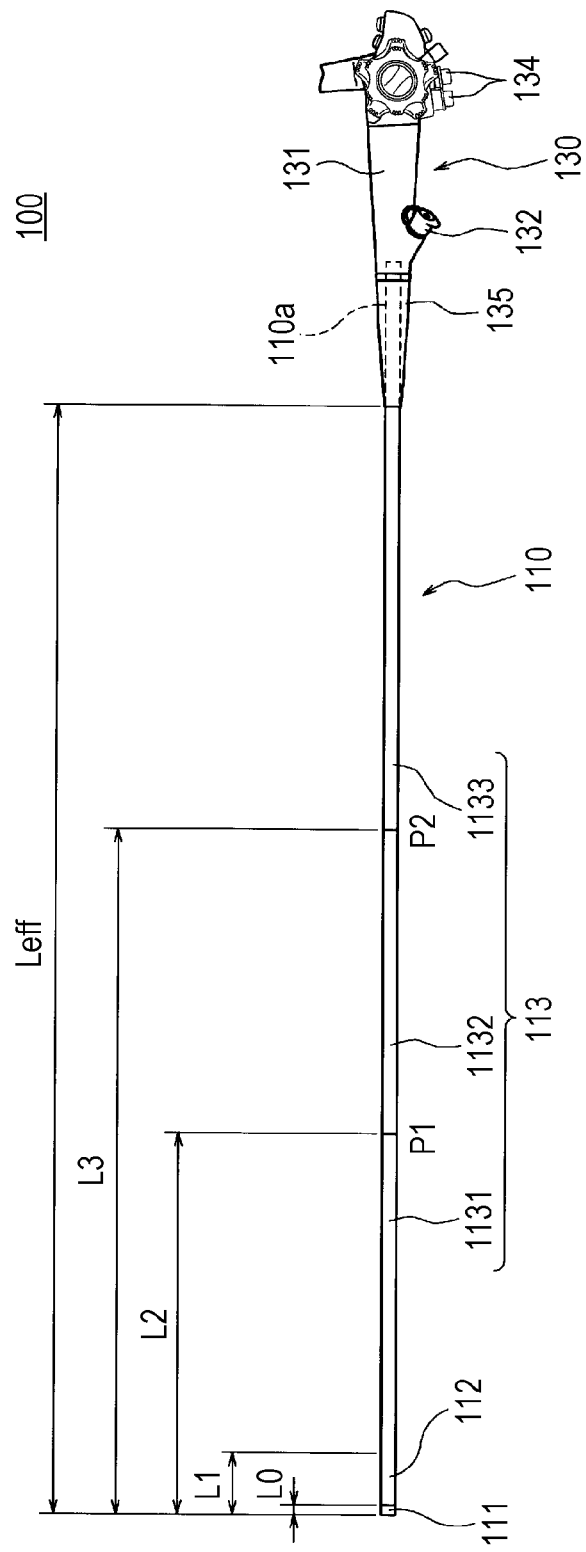
FIG. 22 is an explanatory diagram illustrating a configuration of an insertion portion of an endoscope according to a third embodiment.

FIG. 22 is an explanatory diagram illustrating the configuration of the insertion portion 110 of the endoscope 100 according to the third embodiment. In FIG. 22, the connector cable 140 and the connector unit 150 are not illustrated.

The structure of the insertion portion 110 around the rigidity changing position P1 and the rigidity changing position P2 is similar to that around the rigidity changing position P1 according to the second embodiment or its modification. The structure around the rigidity changing position P1 and the structure around the rigidity changing position P2 may be the same or different.

The portion of the soft portion 113 from the distal tip side to the rigidity changing position P1 forms the first region 1131. Similarly, the portion from the rigidity changing position P1 to the rigidity changing position P2 forms the second region 1132. The portion from the rigidity changing position P2 to the distal tip of the folding portion 135 forms the third region 1133.

Since the distance L0 to the distance L1 and the effective length Leff are the same as those in the second embodiment, the description thereof will be omitted. The distance from the distal tip of the insertion portion 110 to the rigidity changing position P1 is described as L2. The distance from the distal tip of the insertion portion 110 to the rigidity changing position P2 is described as L3. L3 is longer than L2.

Figure 23:
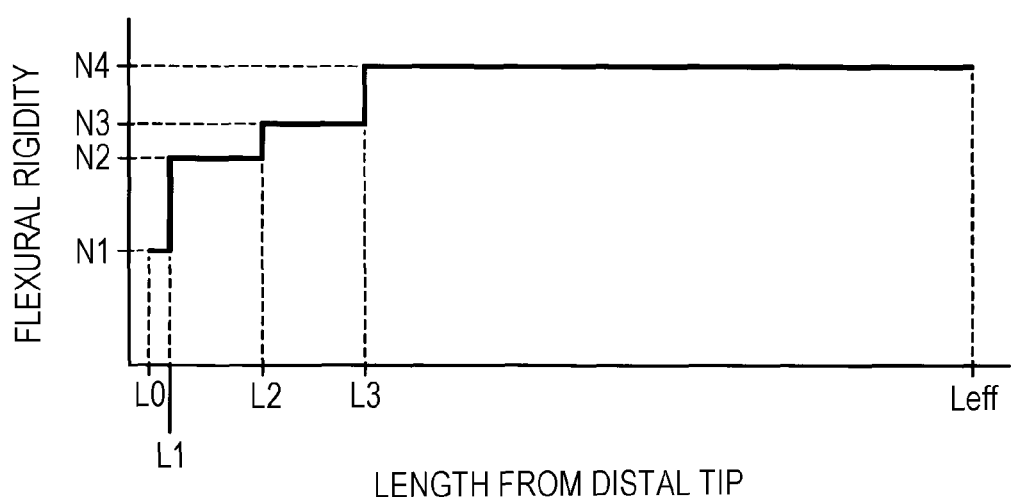
FIG. 23 is a graph for explaining flexural rigidity of a bending section and a soft portion according to the third embodiment.

FIG. 23 is a graph for explaining flexural rigidity of the bending section 112 and the soft portion 113 according to the third embodiment. The horizontal axis represents the length from the distal tip of the insertion portion 110. The vertical axis represents the flexural rigidity of the bending section 112 and the soft portion 113. The flexural rigidity is not defined because the distal tip 111 is rigid.

L0, L1, L2, L3, and Leff indicate the lengths from the distal tip of the insertion portion 110 described using FIG. 22, respectively. N1 indicates the flexural rigidity of the bending section 112. N2 indicates the flexural rigidity of the first region 1131. N3 indicates the flexural rigidity of the second region 1132. N4 indicates the flexural rigidity of a third region 1133. N1, N2, N3, and N4 satisfy the relationship of Expression (2).

$$N1 < N2 < N3 < N4 \quad (2)$$

The method of measuring the flexural rigidity N4 of the third region 1133 is the same as the method of measuring the flexural rigidity N3 of the second region 1132 described in the second embodiment, and thus the description thereof is omitted.

Table 6 indicates an example of the suitable endoscope 100. The unit of the tube outer diameter, L1, L2, L3 and Leff is mm. The unit of N1, N2, N3 and N4 is Newton.

TABLE 6

| No. | 7 | 8 | 9 |
|---|---|---|---|
| Outer diameter of tube | 11.5 | 11.5 | 12.8 |
| L1 | 62 | 104 | 108 |
| L2 | 200 | 300 | 300 |
| L3 | 350 | 1000 | 1000 |
| Leff | 1250 | Lc | |
| N1 | 5 | 2.25 | 2.5 |
| N2 | 9 | 5.5 | 5.75 |
| N3 | 10.5 | 9.5 | 8.5 |
| N4 | 13 | 11 | 10.5 |

Lc is 1300, 1500, or 1700.

No. 7 indicates an example of the endoscope 100 for duodenum. The endoscope 100 for duodenum often adopts a so-called side-view type configuration having an observation window 24, an illumination window 27, the forceps port 121a, and the like on the side surface of the distal tip 111. Since the side-view endoscope 100 has been conventionally used, the illustration of the configuration of the distal tip 111 is omitted. L0 of No. 7 is about 31 mm.

No. 8 and No. 9 indicate examples of the endoscope 100 for the large intestine. As indicated in the bottom of Table 6, for each of No. 8 and No. 9, there are three variations in effective length Leff of 1300 mm, 1500 mm and 1700 mm. L0 of No. 8 and No. 9 is about 10 to 20 mm.

According to this embodiment, since the flexural rigidity changes at two locations, it is possible to provide the endoscope 100 that is easy for the user to insert it into the patient even at a site that is difficult to insert, such as the sigmoid colon, the spleen curve, and the liver curve. The flexural rigidity may change at three or more places.

Note that No. 7 to No. 9 are all examples, and the specifications and uses of the endoscope 100 are not limited to these.

Fourth Embodiment

This embodiment relates to the endoscope 100 in which the flexural rigidity of the soft portion 113 is uniform. Descriptions regarding common parts with the second embodiment will be omitted.

Figure 24:
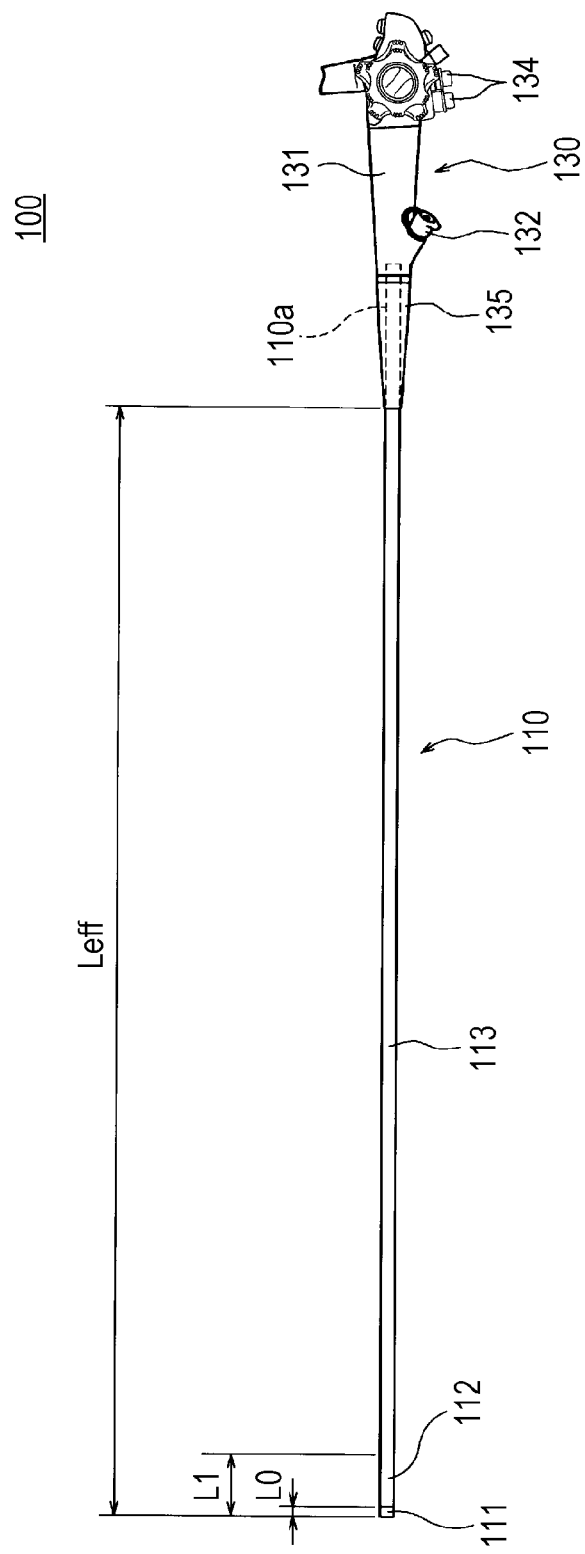
FIG. 24 is an explanatory diagram for explaining a configuration of an insertion portion of an endoscope according to a fourth embodiment.

FIG. 24 is an explanatory diagram for explaining the configuration of the insertion portion 110 of the endoscope 100 according to the fourth embodiment. In FIG. 24, the connector cable 140 and the connector unit 150 are not illustrated. The endoscope 100 of this embodiment does not have the rigidity changing position P1. Since the distance L0 to the distance L1 and the effective length Leff are the same as those in the second embodiment, the description thereof will be omitted.

Figure 25:
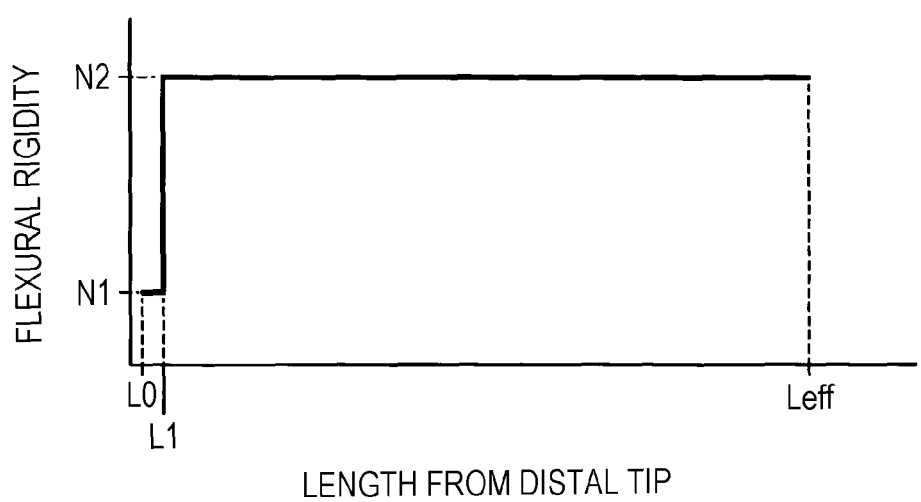
FIG. 25 is a graph for explaining flexural rigidity of a bending section and a soft portion according to the fourth embodiment.

FIG. 25 is a graph for explaining flexural rigidity of the bending section 112 and the soft portion 113 according to the fourth embodiment. The horizontal axis represents the length from the distal tip of the insertion portion 110. The vertical axis represents the flexural rigidity of the bending section 112 and the soft portion 113. The flexural rigidity is not defined because the distal tip 111 is rigid.

L0, L1, and Leff indicate the lengths from the distal tip of the insertion portion 110 described using FIG. 22, respectively. N1 indicates the flexural rigidity of the bending section 112. N2 indicates the flexural rigidity of the soft portion 113. N1 and N2 satisfy the relationship of Expression (3).

$$N1 < N2 \quad (3)$$

Table 7 indicates an example of a suitable endoscope 100. The unit of the tube outer diameter, L1 and Leff is mm. The unit of N1 and N2 is Newton. L0 is about 10 mm to 20 mm.

TABLE 7

| No. | 10 | 11 | 12 |
|---|---|---|---|
| Outer diameter of tube | 3.7 | 2.7 | 3.3 |
| L1 | 31 | 25 | 30 |
| Leff | 300 | 1900 | 600 |
| N1 | 0.8 | 1 | 1.25 |
| N2 | 2 | 2.25 | 5 |

No. 10 indicates the endoscope 100 for a respiratory organ. Compared to the endoscope 100 for a respiratory organ indicated in No. 4, the diameter is smaller, the effective length Leff is shorter, and the flexural rigidity is smaller. It is possible to provide the endoscope 100 that can be easily inserted even in a patient with a narrow trachea such as children.

No. 11 indicates a so-called baby scope endoscope 100. Compared with the endoscope 100 for baby scope indicated in No. 6, the diameter is smaller and the flexural rigidity is smaller. It is possible to provide the endoscope 100 for a baby scope which can be combined with the endoscope 100 for a duodenum having a channel diameter smaller than that of No. 6.

No. 12 indicates the endoscope 100 for endotracheal intubation used for inserting a tracheal tube when performing general anesthesia. For endotracheal intubation, for example, the respiratory endoscope 100 described in No. 4 may be used. However, in endotracheal intubation, it is not necessary to insert the endoscope 100 up to the bronchus. Therefore, for endotracheal intubation, as illustrated in No. 12, the endoscope 100 in which the flexural rigidity of the entire insertion portion 110 is uniform can be used.

Note that No. 10 to No. 12 are all examples, and the specifications and uses of the endoscope 100 are not limited to these.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the invention is defined not by the above-described meaning but by claims, and intends to include all modifications within meaning and a scope equal to claims.

(Appendix 1)
An endoscope comprising:
an insertion portion including an imaging unit; and
an operation unit for bending a part of the insertion portion,
wherein at least a part of the insertion portion is configured by a resin tube,
wherein the tube has a plurality of resin channels forming the tube,
wherein the insertion portion includes a distal tip including the imaging unit, a bending section that is bent by the operation unit, and a soft portion between the bending section and the operation unit,
wherein at least a part of the bending section and the soft portion is configured by the tube,
wherein a Shore A hardness of the resin is A30 or more and A95 or less,
wherein a rigid member inserted into the channel, and an angle wire inserted into the rigid member and connected to a bending mechanism of the bending section are included, and
wherein the operation unit is provided to operate the angle wire.

(Appendix 2)
The endoscope according to Appendix 1, wherein the Shore A hardness of the resin in the bending section is lower than the Shore A hardness of the resin in the soft portion.

(Appendix 3)
The endoscope according to Appendix 1 or 2, wherein the Shore A hardness of the resin changes in an axial direction or a radial direction of the tube.

(Appendix 4)
The endoscope according to Appendix 1, wherein the rigid member has a flexural rigidity higher than that of the tube, and is inserted into the channel in the soft portion.

(Appendix 5)
The endoscope according to any one of Appendices 1 to 4, wherein the insertion portion has a fractured portion that is fractured when the imaging unit is removed.

(Appendix 6)
An endoscope comprising an insertion portion including an imaging unit and an operation unit for bending a part of the insertion portion,
wherein at least a part of the insertion portion is configured by a resin tube,
wherein the tube has a plurality of resin channels forming the tube,
wherein the insertion portion includes a distal tip including the imaging unit, a bending section that is bent by the operation unit, and a soft portion between the bending section and the operation unit,
wherein at least a part of the bending section and the soft portion is configured by the tube,
wherein a Shore A hardness of the resin is A30 or more and A95 or less,
wherein a single-use portion including the tube that is replaced after each use, and a reusable portion including the imaging unit that is collected and reused for each use are included.

(Appendix 7)
The endoscope according to Appendix 6, wherein the Shore A hardness of the resin changes in an axial direction or a radial direction of the tube.

(Appendix 8)
The endoscope according to Appendix 6 or 7, wherein the Shore A hardness of the resin in the bending section is lower than the Shore A hardness of the resin in the soft portion.

(Appendix 9)
The endoscope according to any one of Appendixes 6 to 8, comprising a rigid member inserted into the channel, and an angle wire inserted into the rigid member and connected to a bending mechanism of the bending section,
wherein the operation unit is provided to operate the angle wire.

(Appendix 10)
The endoscope according to Appendix 9, wherein the rigid member has a flexural rigidity higher than that of the tube, and is inserted into the channel in the soft portion.

(Appendix 11)
The endoscope according to any one of Appendixes 6 to 10, wherein the insertion portion has a fractured portion that is fractured when the imaging unit is removed.

REFERENCE SIGNS LIST 1 endoscope system
2 monitor
3 processor 24 observation window
27 illumination window
31 treatment tool channel
32 air supply channel
33 water supply channel
34 auxiliary water supply channel
35 wire channel
36 cable channel
41 angle wire
411 retaining portion
42 wire sheath (rigid member)
44 cable
51 outer cover
511 first outer cover
512 second outer cover
516 thin region
517 thick region
54 second fixing protrusion
100 endoscope
110 insertion portion
110a tube
110b channel
110c power source connector
110d signal connector
110e holding block
111 distal tip
112 bending section
112a opening
112b opening
112c opening
112d opening
113 soft portion
1131 first region
1132 second region
1133 third region
114 fractured portion
120 imaging unit
121 body portion
121a forceps port
121b air supply port
121c water supply port
121d auxiliary water supply port
122 power source pin
123 signal pin
124 image sensor
125 objective lens
126 lens
127 small LED illumination
130 operation unit
131 operation unit body
132 treatment tool inlet
133 bending operation knob
134 switches
135 folding portion
140 connector cable
150 connector unit
R reusable portion
S single-use portion
P1 rigidity changing position
P2 rigidity changing position

The invention claimed is:

1. An endoscope, comprising:
an insertion portion;
an operation unit; and
a fracturable portion,
wherein the insertion portion includes
a single-use portion including a tube that is provided with a plurality of channels penetrating in a longitudinal direction, wherein the operation unit is connected to one end of the tube, and
a reusable portion including a distal tip that covers another end of the tube and has a plurality of through holes that communicate with a respective said plurality of channels, and
wherein the fracturable portion is adhered to and covers a joint between the tube and the distal tip,
wherein the fracturable portion is configured to be fractured when the single-use portion and the reusable portion are separated,
wherein an outermost diameter of the tube and an outermost diameter of the distal tip are the same where the tube and distal tip are covered by the fracturable portion, and
wherein the material at the outermost diameter of the tube not covered by the fracturable portion is harder or more rigid than the material of the fracturable portion.

2. The endoscope according to claim 1,
wherein the distal tip includes an image sensor, and
wherein the insertion portion includes a power source cable that is inserted into one of the plurality of channels, and supplies power to the image sensor.

3. The endoscope according to claim 1,
wherein the distal tip includes an image sensor, and
wherein the insertion portion includes a signal cable that is inserted into one of the plurality of channels and transfers a signal with respect to the image sensor.

4. The endoscope according to claim 3,
wherein the signal cable is inserted into the same channel as a power source cable that supplies power to the image sensor.

5. The endoscope according to claim 1,
wherein the insertion portion includes
a wire sheath that is inserted into a part of the plurality of channels and is fixed to the operation unit, and
an angle wire that penetrates through the wire sheath and has an end portion on a distal tip side protruding from the wire sheath and fixed to a distal tip of the tube,
wherein the distal tip covers an end portion of a channel into which the wire sheath is inserted, and
wherein the operation unit includes a bending mechanism that is connected to another end of the angle wire and is provided to push and pull the angle wire.

6. The endoscope according to claim 5,
wherein the insertion portion includes
a first region adjacent to a bending section that is bendable, and
a second region adjacent to the first region and having a flexural rigidity larger than that of the first region.

7. The endoscope according to claim 6,
wherein the first region is longer than the bending section.

8. The endoscope according to claim 6,
wherein the second region is longer than the first region.

9. The endoscope according to claim 6,
wherein the second region has a uniform flexural rigidity along a longitudinal direction.

10. The endoscope according to claim 6,
wherein the first region has a uniform flexural rigidity along a longitudinal direction.

11. The endoscope according to claim 6,
wherein the insertion portion has a third region adjacent to the second region and having a flexural rigidity larger than that of the second region.

12. The endoscope according to claim 11, wherein the third region is longer than the second region.
13. The endoscope according to claim 11, wherein the third region has a uniform flexural rigidity along a longitudinal direction.
14. The endoscope according to claim 1, wherein the fracturable portion covers one end of the distal tip adjacent to the joint and does not protrude beyond another end of the distal tip.

* * * * *